US005679650A

United States Patent [19]
Fukunaga et al.

[11] Patent Number: 5,679,650
[45] Date of Patent: Oct. 21, 1997

[54] PHARMACEUTICAL COMPOSITIONS INCLUDING MIXTURES OF AN ADENOSINE COMPOUND AND A CATECHOLAMINE

[76] Inventors: Atsuo F. Fukunaga; Alex S. Funuknaga, both of 5411 Littlebow Rd., Rancho Palos Verdes, Calif. 90274

[21] Appl. No.: 341,668

[22] Filed: Nov. 17, 1994

Related U.S. Application Data

[63] Continuation-in-part of Ser. No. 158,012, Nov. 24, 1993, abandoned.

[51] Int. Cl.$^6$ ............... A61K 31/70; A61K 31/135; C07H 19/167; C07H 211/00
[52] U.S. Cl. ............... 514/46; 514/47; 514/221; 514/258; 514/261; 514/270; 514/282; 514/399; 514/653; 514/731; 536/26.23; 536/26.256; 536/26.27; 536/27.6; 564/374
[58] Field of Search ............... 514/43, 45, 46, 514/47, 221, 258, 261, 270, 282, 399, 653, 731; 564/374; 536/27.13, 27.6, 27.61, 27.62, 27.63, 26.26, 26.23, 27.7

[56] References Cited

U.S. PATENT DOCUMENTS

| | | | |
|---|---|---|---|
| 4,088,756 | 5/1978 | Voorhees | 514/47 |
| 4,514,405 | 4/1985 | Irmscher et al. | 514/46 |
| 4,590,180 | 5/1986 | Irmscher et al. | 514/46 |
| 4,605,644 | 8/1986 | Foker | 514/45 |
| 4,673,563 | 6/1987 | Berne et al. | 514/45 |
| 4,693,996 | 9/1987 | Steffen | 514/46 |
| 4,880,783 | 11/1989 | Mentzer, Jr. et al. | 514/46 |
| 4,880,918 | 11/1989 | Rapaport | 514/46 |
| 4,980,379 | 12/1990 | Belardinelli et al. | 514/263 |
| 5,049,372 | 9/1991 | Rapaport | 424/1.77 |
| 5,070,877 | 12/1991 | Mohiuddin et al. | 128/653.4 |
| 5,104,859 | 4/1992 | Sollevi | 514/46 |
| 5,137,712 | 8/1992 | Kask et al. | 424/10 |
| 5,206,222 | 4/1993 | Forman et al. | 514/46 |
| 5,236,908 | 8/1993 | Gruber et al. | 514/46 |
| 5,364,862 | 11/1994 | Spada et al. | 514/303 |

FOREIGN PATENT DOCUMENTS

| | | |
|---|---|---|
| 797237 | 6/1958 | United Kingdom . |
| 2171305 | 8/1986 | United Kingdom . |
| 9102951 | 7/1991 | WIPO . |

OTHER PUBLICATIONS

Fukunaga, "Intravenous Administration of Large Dosages of Adenosine or Adenosine Triphosphate with Minimal Blood Pressure Fluxuation," *Life Sciences {Pharmacology Letters}*, 56(9), PL209–PL218 (1995).

Waller, J, L., "Inotropes and Vasopressors,", Ch. 12 in Kaplan, J. A. (ed.), *Cardiac Anesthesia, vol. 2, Cardiovascular Pharmacology*, 1983, Grune & Stratton, New York, NY, only pp. 273, 279 and 280 supplied.

Lawson, N. W., "Autonomic Nervous System Physiology and Pharmacology," Ch. 14 in *Clinical Anesthesia*, 2nd Ed., Barash et al. (eds.), J. B. Lippincott Co., Philadelphia, PA, 1992, only chapter title page and p. 357 supplied.

Bourne, H. R., et al., "Drug Receptors and Pharmacodynamics," Ch. 2 in *Basic & Clkinical Pharmacology, 6th Ed.*, Katzung, B. G. (ed.), Appleton & Lange, Norwalk, CN, 1995, only pp. 9 and 17 supplied.

Berkow et al.(eds.), *The Merck Manual, 16th Ed.*, Merck & Co., Rahwah, NJ, 1992, only pp. 441–443 supplied.

Sawynok & Sweeney. "Commentary—The Role of Purines in Nociception," *Neuroscience*, 32(3), 557–569 (1989).

Jacobson et al., "Adenosine Receptors: Pharmacology, Structure–Activity Relationships, and Therapeutic Potential," *J, Medicinal Chemistry*, 35(3), []–422 (1992).

Klement et al., "Adenosine Does Not Evoke Pain From Venous Paravascular Nociceptors in the Humans," *Cardiovascular Research*, 26. 186–189 (1992); only pp. 186–188 supplied.

Harvey, S.C., "Sympathomimetic Drugs," Ch. 43 in *Remington's Pharmaceutical Sciences, 18th Ed.*, Mack Publishing Co., Easton, PA, 1990, pp. 870–888.

Hall et al., "Antiviral Drug and Interferon Combinations," Ch. 3 in *Antiviral Agents: The Development and Assessment of Antiviral Chemotherapy, vol. II*, H. J. Field (ed.), CRC Press, Boca Raton, FL, 1987, pp. 29–43 and 74–77.

Homeister et al., "Combined Adenosine and Lidocaine Administration Limits Myocardial Reperfusion Injury," *Circulation*, 82(2), 595–608 (1990).

Friedholm et al, "The Release of Adenosine and Inosine From Canine Subcutaneous Adipose Tissue by Nerve Stimulation and Noradrenaline," *J. Physiol.*, 313, 351–367 (1981).

Lagercrantz et al., "Adenosine Surge at Birth," Abstract in *Adenosine and Adenine Nucleotides*, D. M. Paton (ed.), Taylor & Francis, 1988, p. 290.

Barraco, "Behavior Actions of Adenosine and Related Substances," Ch. 28 in *Adenosine and Adenine Nucleotides as Regulators of Cellular Function*, J. W. Phillis (ed.), CRC Press, Boca, Raton, FL. 1991, pp. 339–366.

(List continued on next page.)

*Primary Examiner*—John Kight
*Assistant Examiner*—L. Eric Crane
*Attorney, Agent, or Firm*—Fulwider Patton Lee & Utecht, LLP

[57] ABSTRACT

A purine compound, which has a desired and an undesired effect when a dosage sufficient to induce the desired effect is administered to a mammal, is combined with a counteracting agent, wherein the counteracting agent can reduce the undesired effect when the combination containing an effective amount of the purine compound is administered to a mammal. In a preferred embodiment, an adenosine compound is combined in vitro with a catecholamine in a predetermined ratio to form an adenosine composition. Very high dosages of a purine compound, such as adenosine, ATP or their analogs can be administered to a mammal via administration of compositions containing the purine compound and a counteracting agent, while reducing the dangerous, undesired effects associated with administering the same dosage of purine compound without first combining it with the counteracting agent. New catecholamine compositions are also taught. The purine and catecholamine compositions of the present invention pioneer new therapies which take advantage of the diversity of physiological effects of purine and catecholamine compounds.

1 Claim, 17 Drawing Sheets

OTHER PUBLICATIONS

Dragunow, "Adenosine and Epileptic Seizures,", Ch. 29 in *Adenosine and Adenine Nucleotides as Regulators of Cellular Function*, J. W. Phillis (ed.), CRC Press, Boca Raton, FL, 1991, pp. 367–379.

Radulovacki, "Adenosine and Sleep," Ch. 30 in *Adenosine and Adenine Nucleotides as Regulators of Cellular Function*, J. W. Phillis (ed.), CRC Press, Boca Raton, FL, 1991, pp. 381–390.

Sawynok, "Adenosine and Pain," Ch. 31 in *Adenosine and Adenine Nucleotides as Regulators of Cellular Function*, J. W. Phillis (ed.), CRC Press, Boca Raton, FL, 1991, pp. 391–400.

Ng et al., "Adenosine and Asthma," Ch. 32 in *Adenosine and Adenine Nucleotides as Regulators of Cellular Function*, J. W. Phillis (ed.), CRC Press, Boca Raton, FL, 1991, pp. 403–412.

Marangos et al., "Adenosine-Based Therapeutics in Neurologic Disease," Ch. 33 in *Adenosine and Adenine Nucleotides as Regulators of Cellular Function*, J. W. Phillis (ed.), CRC Press, Boca Raton, FL, 1991, pp. 413–422.

K.A. Rudolphi, "Manipulation of Purinergic Tone as a Mechanism for Controlling Ischemic Brain Damage," Ch. 34 in *Adenosine and Adenine Nucleotides as Regulators of Cellular Function*, J. W. Phillis (ed.), CRC Press, Boca Raton, FL, 1991, pp. 423–436.

Burnstock (I), "Overview—Purinergic Mechanisms," in Part I of *Biological Actions of Extracellular ATP, Annals N.Y. Acad. Sci.*, vol. 603, N.Y. Acad. Sci., New York, NY 1990, pp. 1–18.

Pelleg et al., "Cardiac Effects of Adenosine and ATP," in Part I of *Biological Actions of Extracellular ATP, Annals N.Y. Acad. Sci.*, vol. 603, N.Y. Acad. Sci., New York, NY, 1990, pp. 19–30.

Burnstock (II), "Dual Control of Local Blood Flow by Purines," in Part I of *Biological Actions of Extracellular ATP, Annuals N.Y. Acad. Sci.*, vol. 603, N. Y. Acad. Sci., New York, NY, 1990, pp. 31–45.

Williams, "Purine Nucleosides and Nucleotides as Central Nervous System Modulators, Adenosine as the Prototypic Paracrine Neuroactive Substance," in Part I of *Biological Actions of Extracellular ATP, Annals N.Y. Acad. Sci.*, vol. 603, N.Y. Acad. Sci., New York, NY, 1990, pp. 93–107.

Chaudry, "Use of ATP Following Shock and Ischemia," in Part I of *Biological Actions of Extracellular ATP, Annals N.Y. Acad. Sci.*, vol. 603, N.Y. Acad, Sci., New York, NY, 1990, pp. 130–141.

White at al., "Neural Release of ATP and Adenosine," in Part IV of *Biological Actions of Extracellular ATP, Annals N.Y. Acad. Sci.*, vol. 603, N.Y. Acad. Sci., New York, NY, 1990, pp. 287–299.

Kim et al., "ATP Effects on Secretion and Second Messenger Production in Bovine Chromaffin Cells," in Poster Papers section of *Biological Actions of Extracellular ATP, Annals N.Y. Acad. Sci.* vol. 603, N.Y. Acad. Sci., New York, NY, 1990, pp. 435–436.

Forsyth et al., "Purine Modulation of Norepinephrine Release in the Rat Vas Deferens," in Poster Papers section of *Biological Actions of Extracellular ATP, Annals N.Y. Acad. Sci.*, vol. 603, N.Y. Acad. Sci., New York, NY, 1990, pp., 507–509.

Chau et al., "Norepinephrine and ATP as Cotransmitters in the Guinea Pig Portal Vein and Rabbit Saphenous Artery," in Poster Papers section of *Biological Actions of Extracellular ATP, Annals N.Y. Acad. Sci.*, vol. 603, N.Y. Acad. Sci., New York, NY, 1990, pp. 510–512.

Dunwiddie, "Electrophysiological Aspects of Adenosine Receptor Function," Ch. 5 in *Adenosine and Adenosine Receptors*, M. Williams (ed.), Humana Press, 1990, Clifton, NJ, pp. 143–172.

Mullane et al., "Adenosine and Cardiovascular Function," Ch. 8 in *Adenosine and Adenosine Receptors*, M. Williams (ed.), Humana Press, 1990, Clifton, NJ, pp. 289–333.

Griffiths et al., "The Role of Adenosine in Respiratory Physiology," Ch. 10 in *Adenosine and Adenosine Receptors*, M. Williams (ed.), Humana Press, 1990, Clifton, NJ, pp. 381–422.

Jarvis et al., "Adenosine in Central Nervous System Function," Ch. 11 in *Adenosine and Adenosine Receptors*, M. Williams (ed.), Humana Press, 1990, Clifton, NJ, pp. 423–474.

Fredholm et al., "Mechanism(s) of Inhibition of Transmitter Release by Adenosine Receptor Activation," in *Adenosine Receptors in the Nervous System*, Ribeiro (ed.), Taylor & Francis, New York, 1989, pp. 123–130.

Kather, "Beta Adrenergic Receptor Mediated Stimulation of Adenine Nucleotide Catabolism and Purine Release in Human Adipocytes," Ch. 20 in *Purines in Cellular Signaling*, Jacobson et al. (eds.), Springer–Verlag, New York, 1990, pp. 120–125.

Williams, "Adenosine Receptors as Drug Targets: Fulfilling the Promise?" Ch. 27 in *Purines in Cellular Signaling*, Jacobson et al. (eds.), Springer–Verlag, New York, 1990, pp. 174–183.

Westfall et al, "Modulation of Norepinephrine Release by ATP and Adenosine," Ch. 38 in *Purines in Cellular Signaling*, Jacobson et al (eds.), Springer–Verlag, New York, 1990, pp. 260–265.

Howell et al., "Mechanisms of Xanthine Actions in Models of Asthma," Ch. 54 in *Purines in Cellular Signaling*, Jacobson et al. (eds.), Springer–Verlag, New York, 1990, pp. 370–375.

Headrick et al., "Modulation of Cardiac Efficiency: A Role for Adenosine in Metabolism in Metabolically Stimulated Rat Heart," Abstract No. D21 in *Purines in Cellular Signaling*, Jacobson et al. (eds.), Springer–Verlag, New York, 1990, p. 408.

Moritoki, "Evidence for the Involvement of Cyclic GMP in Adenosine–Induced Vasodilation," Ch. 20 in *Role of Adenosine and Adenine Nucleotides in the Biological System, Metabolism, Release, Transport, Receptors, Transduction Mechanisms and Biological Actions*, Imai et al. (eds.), Elsevier Science Publishers BV, Amsterdam, NE, 1991, pp. 218–225.

Schrader et al., "Intra– and Extracellular Formation of Adenosine by Cardiac Tissue," Ch. 24 in *Role of Adenosine and Adenine Nucleotides in the Biological System, Metabolism, Release, Transport, Receptors, Transduction Mechanisms and Biological Actions*, Imai et al. (eds.), Elsevier Science Publishers BV, Amsterdam, NE, 1991, pp. 261–271.

Nakazawa et al., "ATP Pyrophosphohydrolase: A New Pathway of Extracellular Adenosine Formation in the Heart," Ch. 27 in *Role of Adenosine and Adenine Nucleotides in the Biological System, Metabolism, Release, Transport, Receptors, Transduction Mechanisms and Biological Actions,* Imai et al. (eds,), Elsevier Science Publishers BV, Amsterdam, NE, 1991, pp. 302–311.

Belardenelli, "Chronotropic and Dromotropic Effects of Adenosine: Physiological Consequences," Ch. 31 in *Role of Adenosine and Adenine Nucleotides in the Biological System, Metabolism, Release, Transport, Receptors, Transduction Mechanisms and Biological Actions,* Imai et al. (eds.), Elsevier Science Publishers BV, Amsterdam. NE, 1991, pp. 357–368.

Dobson et at., "Adenosine and the Reduced Responsiveness of the Aged Heart to Adrenergic Stimulation," Ch. 33 in *Role of Adenosine and Adenine Nucleotides in the Biological System, Metabolism, Release, Transport, Receptors, Transduction Mechanisms and Biological Actions,* Imai et al. (eds.), Elsevier Science Publishers, BV, Amsterdam, NE, 1991, pp. 377–386.

Hori et al., "Interactions Between α-Adrenergic Activity and Adenosine in Ischemic Hearts," Ch. 34 in *Role Of Adenosine and Adenine Nucleotides in the Biological System, Metabolism, Release, Transport, Receptors, Transduction Mechanisms and Biological Actions,* Imai et al. (eds.), Elsevier Science Publishers BV, Amsterdam, NE, 1991, pp. 387–396.

Xiong et al., "Actions of Endogenous and Exogenous ATP on Vascular Smooth Muscle Cell Membranes," Ch. 35 in *Role of Adenosine and Adenine Nucleotides in the Biological System, Metabolism, Release, Transport, Receptors, Transduction Mechanisms and Biological Actions,* Imai et al. (eds.), Elsevier Science Publisher BV, Amsterdam, NE, 1991, pp. 397–406.

Katsuragi et al., "Neurotransmitter–Mediated ATP Release from Smooth Muscles ," Ch. 36 in *Role of Adenosine and Adenine Nucleotides in the Biological System, Metabolism, Release, Transport, Receptors, Transduction Mechanisms and Biological Actions,* Imai et al. (eds.), Elsevier Science Publishers BV, Amsterdam, NE, 1991, pp. 407–414.

Shirahase et al., "Endothelium–Dependent Cerebrovascular Contraction Induced by Adenine Nucleotides," Ch. 38 in *Role of Adenosine and Adenine Nucleotides in the Biological System, Metabolism, Release, Transport, Receptors, Transduction Mechanisms and Biological Actions,* Imai et al. (eds.), Elsevier Science Publisher BV, Amsterdam, NE, 1991, pp. 424–431.

Pelleg, "The Effects of Adenosine and Adenosine 5'–Triphosphate on Ventricular Pacemakers in the Canine Heart in vivo" Ch. 49 in *Role of Adenosine and Adenine Nucleotides in the Biological System, Metabolism, Release, Transport, Receptors, Transduction Mechanisms and Biological Actions,* Imai et at. (eds.), Elsevier Science Publishers BV, Amsterdam, NE, 1991, pp. 539–546.

Nomura et al., "Possible Involvement of $D_2$ Dopamine Receptors in the $A_1$ Adenosine Receptor–Adenylate Cyclase System in Rat Cerebral Cortex," Ch. 62 in *Role of Adenosine and Adenine Nucleotides in the Biological System, Metabolism, Release, Transport, Receptors, Transduction Mechanisms and Biological Actions,* Imai et al. (eds.), Elsevier Science Publishers BV, Amsterdam, NE, 1991, pp. 673–682.

Sollevi, "Clinical Studies on the Effect of Adenosine," Ch. 48 in *Role of Adenosine and Adenine Nucleotides in the Biological System, Metabolism, Release, Transport, Receptors, Transduction Mechanisms and Biological Actions,* Imai et al. (eds.), Elsevier Science Publishers BV, Amsterdam, NE, 1991, pp. 535–537.

Drury AN, et al: The Physiological activity of adenine compounds with special reference to their action upon the mammalian heart. *Journal of Physiology* (London) 68:213–237, 1929.

Fukunaga AF, et al: Plasma catecholamine levels and circulatory changes during i.v. infusion of ATP and sodium nitropurisside in dogs. *paper presented at the Eight International Congress of Pharmacology, JUPHAR* Jul. 19–24, Tokyo, 1981.

Fukunaga AF, et al: Hemodynamic effects of ATP and nitroprusside. *Anesthesiology* 55:A13, 1981.

Bloor BC, et al: Coronary sinus blood flow during hypotension induced by sodium nitroprusside or adenosine triphosphate infusion. *Anesthesiology* 57:A51, 1982.

Fukunaga AF, et al: ATP–induced hypotensive anesthesia during surgery. *Anesthesiology* 57:A65, 1982.

Fukunaga A.F, et al: Comparative hemodynamic, metabolic and hormonal effects of hypotension induced with ATP and nitroprusside. *Anesthesiology* 57:A64, 1982.

Fukanaga AF, et al: Hypotensive effects of adenosine and adenosine triphosphate compared with sodium nitroprusside. *Anesthesia and Analgesia* 61: 273–278, 1982.

Ma CC, et al: Comparison of hemodynamic responses during hypotension induced by halothane and adenosine triphosphate. *Anethesiology* 57:A67,1982.

Fukunaga AF, et al: Hemodynamic and metabolic changes of ATP–induced hypotension during surgery. *Anesthesiology* 59:A12, 1983.

Ma CC, et al: A comparative study of the sympathetic and the metabolic activities during induced hypotension with adenosine triphosphate and sodium nitroprusside. *Anesthesiology* 59:A10, 1983.

Phillis JW, et al: Roles of adenosine and adenine nucleotides in the central nervous system. In Daly JW et al eds: *Physiology and Pharmacology of Adenosine Derivatives,* New York, Raven Press, 1983.

Durant NN, et al: Potentiation and prolongation of vecuronium neuromuscular block by adenosine triphosphate. *Anesthesiology* 61:A295, 1984.

Fukunaga AF, et al: Dipyridamole potentiates the hypotensive effect of ATP. *Anesthesiology* 61:A39–1984.

Fukunaga AF, et al: ATP attenuates the autonomic and cardiovascular effects of catecholamines in experimental animals. *Anesthesiology* 63:A56, 1985.

Fukunaga AF, et al: Cerebral and liver oxygenation during hemorrhagic and drug induced hypotension. *Anesthesiology* 65:A 570, 1986.

Fukunaga AF, et al: Changes in regional myocardial blood flow and oxygen tension during induced hypotension with nitroglycerine, isoflurane and ATP in subhuman primates. *Anesthesiology* 67:A8, 1987.

Fukunaga AF, et al: Comparative hemodynamic and oxygen transport studies during induced hypotension with ATP, adenosine, nitrosine, nitroprusside, and halothane. *Anesthesiology* 69:A35, 1988.

Paton DM, ed.: Adenosine and Adenine Nucleotides: *Physiology and Pharmacology* London, Taylor & Francis, 1988, title page only.

Fukunaga AF, et al.: Effects of intravenously administered adenosine and ATP on halothane MAC and its reversal by aminophylline in rabbits. *Anesthesiology* 71:A260, 1989.

Ribeiro JA, ed: *Adenosine Receptors in the Nervous System*, London, Taylor & Francis, 1989, title page only.

Dubyak GR, et al. eds: *Biological Actions of Extracellular ATP.* Annals of the New York Academy of Sciences. v. 603, New York, N.Y., Academy of Sciences, 1990, title page and p. 1 only.

Fukunaga AF, et al: intravenous ATP attenuates surgical stress responses and reduces inhalation anesthetic requirements in humans. *Anesthesiology* 73:A400, 1990.

Fukunaga AF, et al: Cardiovascular changes during adenosine induced hypotension for major orthopedic and cerebral aneurysm surgery. *Anesthesis and Analgesis* 70:S117, 1990.

Ginsburg R, et al: Analgesic activity of intravenous adenosine: A comparison of potency with morphine sulfate. *Anesthesiology* 73:A362, 1990.

Jacobson KA, et al eds: *Purines in Cellular Signaling, Targets for New Drugs.* New York, Springer-Verlag, 1990 only title page.

Kikuta Y, et al: Effects of intravenous ATP on enflurane–$N_2O$ MAC in spontaneously breathing rabbits: Assessment of cardio–respiratory effects. *Anesthesiology* 73:A401, 1990.

Olsson RA, et al: Cardiovascular purinoceptors. *Physiological Reviews* 70:761–809, 1990.

William M. Adenosine receptors as drug targets: Fulfilling the promise? In: Jacobson KA, et al eds: *Purines in Cellular Signalling, Targets for New Drugs*, New York, Springer-Verlag, 1990, pp. 174–175 only.

William M. ed: *Adenosine and Adenosine Receptors.* Clifton, N.J., The Humana Press, 1990, title page only.

Daval JL, et al: Physiological and pharmocalogical properties of adenosine: Therapeutic implications, Minireview, *Life Sciences* 49:1435–1453, 1991.

Fukunaga AF, et al: Analgesic effects of intravenous ATP compared to those of morphine sulfate in the rabbit. *Japanese Society of Anesthesiologists 38th meeting Program I–H–3*, 1991.

Jacobson KA, et al: Novel therapeutics acting via purine receptors. *Biochemical Pharmacology* 41:1399–1410, 1991.

Imai S, et al eds: *Role of Adenosine and Adenine Nucleotides in the Biological System: Metabolism, Release, Transport, Receptors, Transduction Mechanisms and Biological Actions.* Proceedings of the 4th International Symposium on Adenosine and Adenine Nucleotides, Lake Yamanaka, Japan, 13–17 May 1990. Elsevier, Amsterdam, 1991, title page only.

Kaneko Y, et al: Intravenous ATP ameliorates cardiovascular and respiratory functions during anesthesia in surgical patients. *Anesthesis and Analgesia* 72:S132, 1991.

Phillis JW, ed: *Adenosine and Adenine Nucleotides as Regulators of Cellular Function.* Boca Raton, CRC Press, 1991, title page and pp. 423 and 428 only.

William M: Purinergic pharmaceuticals for the 1990s. *Nucleosides & Nucleotides* 10:1087–1099, 1991.

Ely SW, et al: Protective effects of adenosine in myocardial ischemia. *Circulation* 85:893–904, 1992.

Fukunaga AF, et al: Anesthetic efficacy of adenosine and ATP compared to $N_2O$ in the experimental animal model: Sympatholytic vs sympathomimetic. *Anesthesiology* 77:A349, 1992.

Fukunaga AF, et al: Adenosine potentiates the sedative effect of midazolam without respiratory depression in rabbits. *Paper presented at the 10th World Congress of Anaesthesiologists.* Hague, 1992.

Fukunaga AF, et al: Assessment and characterization of the anesthetic effects of intravenous adenosine in the rabbit. *Anesthesia and Analgesia* 74:S103, 1992.

Fukunaga AF, et al: Anesthetic effects of adenosine and ATP in animals and in humans. *International Journal of Purine and Pyrimidine Research* 3:50, 1992.

Kaneko Y, et al: Intravenous ATP potentiates the sedative and hypogenic effects of midazolam in man. *Anesthesiology* 77:A9, 1992.

Kikuta Y, et al: Hemodynamic stability during ATP and midazolam–$N_2O$ balanced anesthesia in surgical patients. *Paper presented at the 10th World Congress of Anesthesiologists,* Hague, 1992.

Miller LP, et al: Therapeutic potential for adenosine receptor activation in ischemic brain injury, *Journal of Neurotrauma* 9(Supp 2): S563–S577, 1992.

Rudolphi KA, et al: Neuroprotective role of adenosine in cerebral ischaemia. *Trends in Pharmacological Sciences* 13:439–445. 1992.

Berne RM: Adenosine—a cardioprotective and therapeutic agent. *Cardiovascular Research* 27:2, 1993.

Downey JM, et al: Spotlight on the cardioprotective properties of adenosine. *Cardiovascular Research* v.27, No. 1, 1993 (only title page supplied).

Downey JM, et al: Adenosine and the anti-infarct effects of preconditioning. Short review. *Cardiovascular Research* 27:3–8, 1993.

Jimura O, et al eds: Spotlight on preconditioning. *Cardiovascular Research* v. 27, No.4 (whole issue), 1993 title page only.

Parratt J: Endogenous myocardial protective (antiarrhythmic) substances. Review article. *Cardiovascular Research* 27:693–702, 1993, p. 702 missing.

George A. Pantely, M.D., et al. Article Adenosine "Renewed Interest in an Old Drug" Circulation 1990; 82:1854–1856.

Clayton L. Thomas, M.D., M.P.H. "Taber's Cyclopedic Medical Dictionary" edited by Clayton L. Thomas, M.D., M.P.H.—Edition 16 Illustrated 1989, p. 203.

F. Gonzales Miranda, et al., "Implicaciones anestesicas del sistema purinergico: revision" Rivista Espanola de Anestesiologia y Reanimacion, vol. 33, No. 1, pp. 25–28, Feb. 1986 (See abstract).

J.D. Loeser "Herpes zoster and postherapetic neuralgia", Pain, vol. 25, No. 2, pp. 149–164, May 1986 (Amsterdam, NL), (See p. 153).

M. Doi, et al., "Sevoflurane anesthesia with adenosine triphosphate for resection of pheochromocytoma", Anesthesiology, vol. 70, No. 2, pp. 360–363, Feb. 1989, Am. Soc. of Anesthesiologists, Inc. (US), see whole article.

T. Hedner, et al.: "Characterization of adenosine–induced respiratory depression in the preterm rabbit", Biology of the Neonate, vol. 47, No. 6, pp. 323–332, (Basel, CH), 1985.

C.N. Paidas, et al.: "Adenosine triphosphate: a potential therapy for hypoxic pulmonary hypertension", Journal of Pediatric Surgery, vol. 23, No. 12, pp. 1154–1160, Dec. 1988, Grune & Stratton (US), see abstract.

J. Nordenberg, et al.: "Exogenous ATP antagonizes the actions of phospholipase A2, local anesthetics, Ca2+ ionophore A23187, and lithium on glucose–1, 6–bisphosphate levels and the activities of phosphofructokinase and phosphoglucomutase in rat muscle", Biochem. Med. Metab. Biol., vol. 38, no. 3, pp. 278–291, Dec. 1987 (US), see p. 284.

Dunwiddie, et al., "Sedative and Anticonvulsant Effects of Adenosine Analogs Compounds in Mouse and Rat" Journal of Pharmacology and experimental Therapeutics, vol. 220, pp. 70–76 issued 1982, (entire document).

Seitz, et al., "Adenosine Reduces Halothane MAC in Dogs," Anesthesiology, vol. 68, issued 1989, (U.S.A.), abstract A264, whole document.

Gomaa, "Characteristic of analgesia Induced by Adenosine Triphosphate", Pharmacology & Toxicology, vol. 61, pp. 199–202, issued 1987, (U.S.A.), whole document.

Rosenthal, "At Surgery's Frontier: Suspended Animation," The New York Times, pp. C1 and C12, issued Nov. 1990, whole document.

Doi, et al., "Spinal Antinociceptive Effects of Adenosine Compounds in Mice," European J. of Pharmacology, vol. 137, pp. 227–231, issued 1987 (Europe).

Aran S, Porter NM, Proudfit HK: Potentiation of the antinociceptive effect of norepinephrine by the adenosine analog, 5'-N-ethylcarboxamide adenosine. Soc Neurosci Abstr 11: 130, 1985.

Aran S, Proudfit HK: Antinociception produced by interactions between intrathecally administered adenosine agonists and norepinephrine. Brain Res 513:255–263, 1990.

Birch BD, Louie GL, Vickery RG, Gaba DM, Maze M: L–Phenylisopropyladenosine (L–PIA) diminishes halothane anesthetic requirements and decreases noradrenergic neurotransmission in rats. Life Sci 42:1355–1360, 1988.

Choca JI, Proudfit HK, Green RD: Identification of $A_1$ and $A_2$ adenosine receptors in the rat spinal cord. J Pharmacol Exp Therap 242:905–910, 1987.

Fredholm BB: Adenosine and central catecholamine neurotransmission. In: Stefanovich V, Rudolphi K, Schubert P eds: Adenosine: Receptors and Modulation of Cell Function. Oxford, IRL Press, 1985. pp. 91–106.

Gatell JA, Barner HB, Shevde K: Adenosine and myocardial protection. J. Cardiothorac Vasc Anesth 7:466–80. 1993.

Janier MF, Vanoverschelde JL, Bergmann SR: Adenosine protects ischemic and reperfused myocardium by receptor–mediated mechanisms. Am J Physiol 264 (1 Pt 2): H163–70, 1993.

Karlsten R, Kristensen JD, Gordh T: R–Phenylisoprophy–l–adenosine increases spinal cord blood flow after intrathecal injection in the rat. Anesth Analg 75:972–976, 1992.

Mullane K: Acadesine: the prototype adenosine regulating agent for reducing myocardial ischaemic injury. Cardiovasc Res 27:43–47, 1993.

Murata K, Sodeyama O, Ikeda K, Fukunaga AF: Prevention of hypertensive crisis with ATP during anesthesia for pheochromocytoma. J Anesth 1:162–167, 1987.

Ocana M, Baeyens JM: Role of ATP–sensitive $K^+$ channels in antinociception induced by R–PIA, an adenosine $A_1$ receptor agonist. Naunyn–Schmiedeberg's Arch Pharmacol 350:57–62, 1994.

Rudolphi KA, Schubert P, Parkinson FE, Fredholm BB: Neuroprotective role of adenosine in cerebral ischaemia. Trend Pharmacol Sci 13:439–445, 1992.

Seitz PA, ter Riet M, Rush W, Merrell WJ: Adenosine decreases the minimum alveolar concentration of halothane in dogs. Anesthesiology 73:990–994, 1990.

Tseng CJ, Ho WY, Lin HC, Tung CS, Kuan CJ: Modulatory effects of endogenous adenosine on epinephrine secretion from the adrenal medulla of the rat. Hypertension 24:714–718, 1994.

Van Belle H: Nucleoside transport inhibition: a therapeutic approach to cardioprotection via adenosine? Cardiovasc Res 27:68–76, 1993.

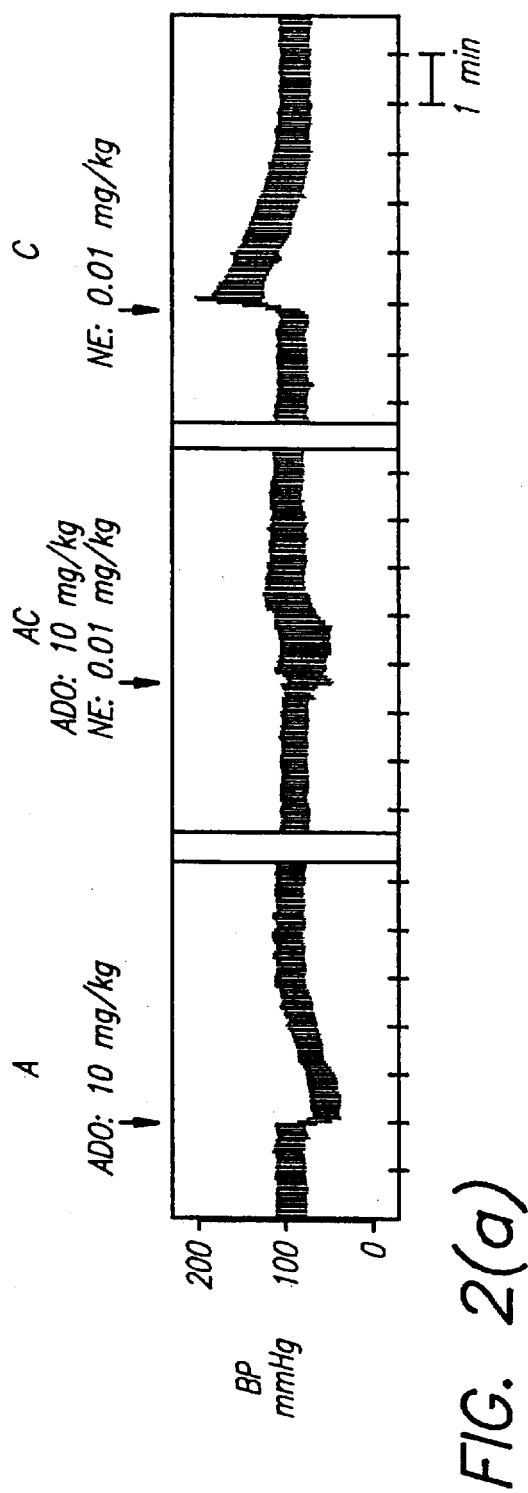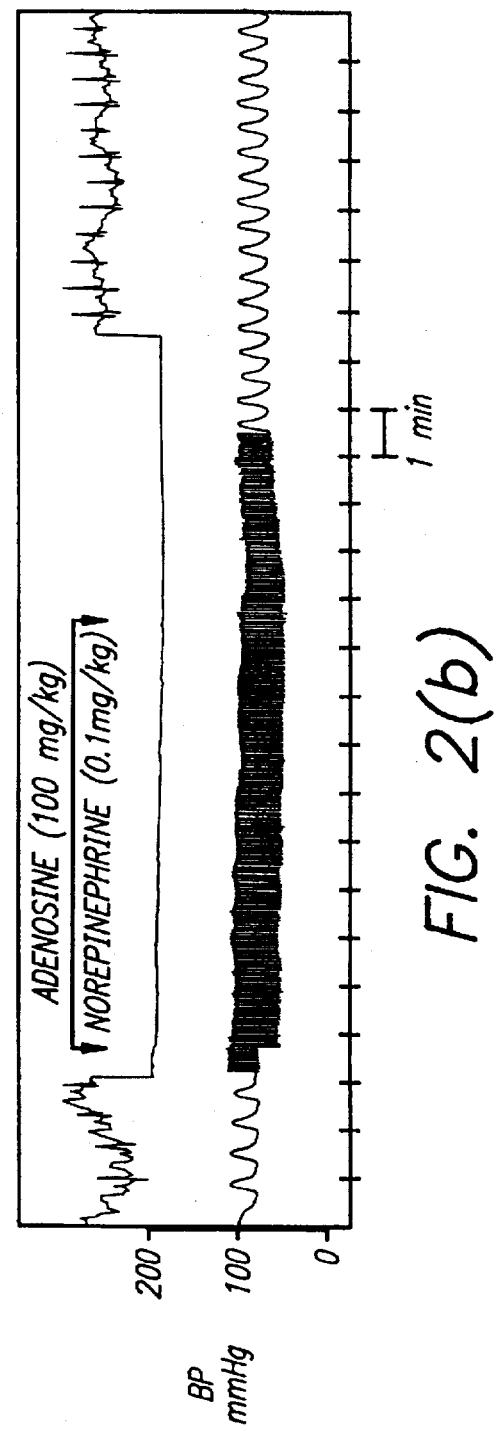
FIG. 2(a)
FIG. 2(b)

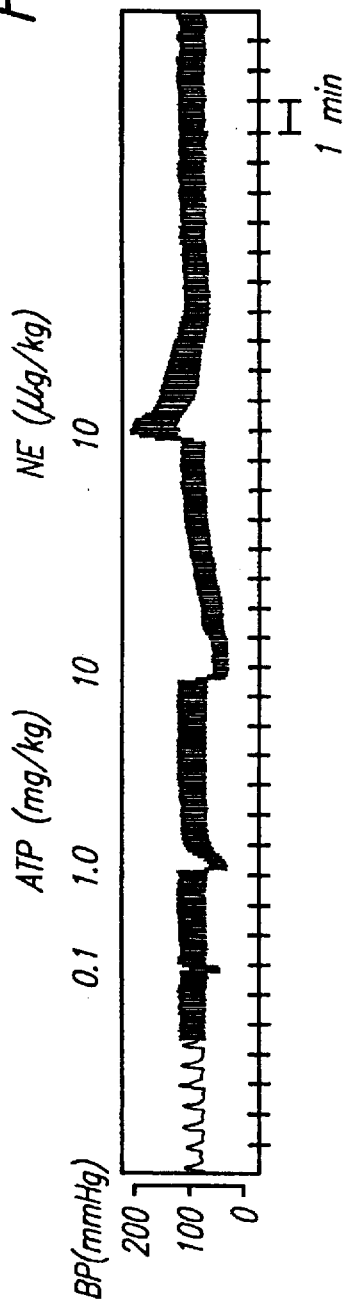
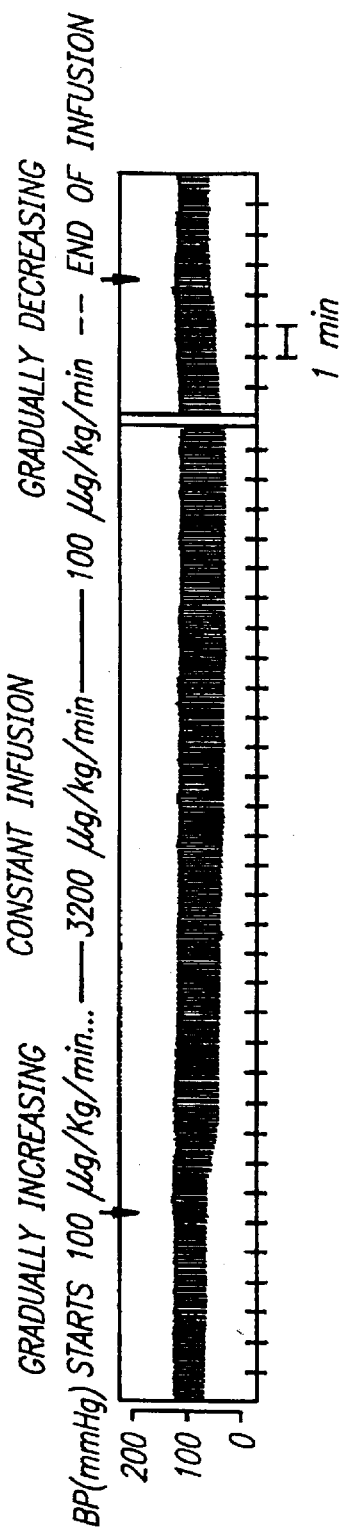
FIG. 4(a)
FIG. 4(b)

PHARMACEUTICAL COMPOSITIONS INCLUDING MIXTURES OF AN ADENOSINE COMPOUND AND A CATECHOLAMINE

RELATED APPLICATIONS

This application is a continuation-in-part of U.S. Ser. No. 08/158,012, filed Nov. 24, 1993, now abandoned, which is related to allowed application U.S. Ser. No. 08/437,080, filed May 5, 1995, which is a continuation of U.S. Ser. No. 08/203,670, filed Feb. 28, 1994, now abandoned, which is a continuation of U.S. Ser. No. 08/003,214, filed Jun. 25, 1993, now abandoned, all of which are incorporated herein by reference.

Ser. No. 08/083,214, filed Jun. 25, 1993, now abandoned, is a continuation of U.S. Ser. No. 07/756,480, filed Sep. 9, 1991, now abandoned, which is a continuation-in-part of U.S. Ser. No. 07/521,529, filed May 10, 1990, now abandoned.

FIELD OF THE INVENTION

The present invention is directed to medicinal compositions and methods for their administration, and more particularly is directed to purine containing compositions, methods for producing purine containing compositions, and methods for administration of same. In another aspect, the present invention is directed to catecholamine containing compositions, methods for producing catecholamine containing compositions, and methods for administration of same.

BACKGROUND OF THE INVENTION

Purine compounds are found in mammalian organisms both intracellularly and extracellularly, and play vital roles in metabolic processes. A nonlimiting example of the ubiquitous nature of purine compounds in mammalian systems is the purine containing nucleoside adenosine, which was reported over 60 years ago to relax coronary vascular smooth muscle and to impair atrioventricular conduction; adenosine has also been found to have antinociceptive properties and has recently been proven to be useful as an anesthetic. The widespread actions of adenosine include effects on the cardiovascular, nervous, respiratory, gastrointestinal, renal and reproductive systems, as well as on blood cells, adipocytes, and immune systems. Very small doses of adenosine (0.01–0.25 mg/kg), provided as a single bolus injection, have been suggested for the treatment of supraventricular tachycardia. A continuous intravenous infusion of up to 0.2 mg/kg/min adenosine for a duration of about 6 minutes has been also suggested for use in diagnostic myocardial imaging. Likewise, the phosphorylated adenosine nucleoside, or adenosine nucleotide, has also been found useful in inducing an anesthetic effect (a phosphorylated nucleoside is a nucleotide). Use of adenosine compounds in anesthesia is discussed in more detail in co-pending U.S. patent application Ser. No. 08/437,080, which is a continuation of Ser. No. 08/083,214, entitled THERAPEUTIC USE OF ADENOSINE COMPOUNDS. The method described in application Ser. No. 08/437,080, which is a continuation of Ser. No. 08/083,214 involves a great improvement in anesthesia by administering up to 5 mg/kg/min adenosine or ATP to a mammal via a continuous infusion; the dosage is adjusted in response to cardiovascular changes which are due to surgical stimulation. At the dosages used, the anesthetic effect is slowly induced, and the patient must be carefully monitored. It is believed that the slow induction of an anesthetic effect is due to the low dosage of adenosine provided, but it was not believed safe to increase the dosages to more quickly achieve an anesthetic effect.

It is believed that the activity of purine compounds is mediated by cell surface receptors specific for a particular purine compound. Depending on a compound and its receptor, binding of the compound to the receptor can be reversible, and have a variety of effects. Further, it is believed that certain compounds can bind to more than one receptor in a competitive fashion with other compounds. In a process, sometimes referred to as biofeedback, the binding of a first compound to a particular receptor or the presence of a first compound may induce the body to produce another agent which counteracts one or more of the effects of the first compound. For example, endogenous substances known as catecholamines, such as those produced by the nerve endings and the adrenal glands, may be released in response to a stressful situation (e.g., norepinephrine, epinephrine, and dopamine). For example, the endogenous production/release of tiny amounts of catecholamines causes increased heart rate and vasoconstriction, which the body responds to by the production of tiny amounts of adenosine and ATP which are believed to counteract certain of the effects of the increased endogenous catecholamines by different receptor mechanisms.

Considerable research has been directed to purine compounds since Drury and Szent-Gyorgyi reported in 1929 on the physiological actions of adenosine on cardiovascular function. Several classes of purine receptors have been identified, and adenosine and adenosine triphosphate, ATP, have been demonstrated as endogenous protective substances. Although certain purine compounds have significant beneficial physiological capabilities, the aforementioned ubiquitous nature and effects of purine compounds also tends to make it difficult to use them therapeutically. In other words, administration of purine compounds to a mammal will have both desired and undesired effects depending on patient physiology and the dosages provided.

Furthermore, because these purine compounds such as adenosine are considered toxic at concentrations that have to be administered to a patient to maintain efficacious extracellular therapeutic level, the administration of adenosine alone has been considered of no use or limited therapeutic use. Therefore, pharmacologists have directed their efforts to achieving high local extracellular level of adenosine by a) inhibiting the uptake of adenosine with reagents that specifically block adenosine transport; b) prevention of the metabolic degradation of adenosine; c) the use of adenosine analogs which will bind to specific adenosine receptors; and recently d) the use of adenosine via its precursor, AICA riboside, which has been the subject of a number of publications and patents (U.S. Pat. Nos. 5,082,829; 5,132,291; 5,187,162; 5,200,525; 5,236,908). However, the above approaches still have major disadvantages associated with their use. The metabolic and uptake blocker strategy is very much restricted in character due to the limited ability of tissue to generate purine compounds, and the adenosine agonist approach has the substantial peripheral side effects associated with these agents, such as hypotension, bradycardia, etc. Thus, despite all the intense efforts in basic sciences and pharmaceutical research, to this date, there has been little success in developing agents that can be used as therapeutic drugs to fully activate purine receptors without side effects. Therefore, until now, there has been no successful medical treatment for prevention or treatment of ischemic damage.

For more information on purine compounds and purine receptor agonists, see Ely et al., "Protective Effects of Adenosine in Myocardial Ischemia", *Circulation*, 85: 893–904 (1992); Miller et al., "Therapeutic Potential for Adenosine Receptor Activation in Ischemic Brain Injury," *J. Neurotrauma*, 9: 563–77 (1992); Williams, "Adenosine Receptors as Drug Targets: Fulfilling the Promise?," in Jacobson et al., Ed., *Purine in Cellular Signaling: Targets for New Drugs*, New York, Springer-Verlag (1990)(See particularly page 175); Lawson et al., "Preconditioning: State of the Art Myocardial Protection," *Cardiovascular Research*, 27:542–50 (1993); Rudolphi, "Manipulation of Purinergic Tone as Mechanism for Controlling Ischemic Brain Damage," in Phillis, J. W., Ed., *Adenosine and Adenine Nucleotides as Regulators of Cellular Function*, Boca Raton, CRC Press (1991); Berne, R., "Adenosine—a Cardioprotective and Therapeutic Agent," *Cardiovascular Research*, 27:2 (1993); Phillis et al., "Roles of Adenosine and Adenine Nucleotides in the Central Nervous System," in Daly et al., Eds., *Physiology and Pharmacology of Adenosine Derivatives*, Raven Press, New York (1983); Galinanes, "Should Adenosine Continue To Be Ignored As A Cardioprotective Agent In Cardiac Operations?," *Journal of Thoracic and Cardiovascular Surgery*, 105: 180–183 (1993); Jacobson et al , "Novel Therapeutics Acting Via Purine Receptors," *Biochemical Pharmacology* 41:1399–1410 (1991); U.K. Patent 797,237; U.S. Pat. No. 4,514,405; U.S. Pat. No. 4,590,180; U.S. Pat. No. 4,605,644; U.S. Pat. No. 4,673,563; U.S. Pat. No. 4,880,783; U.S. Pat. No. 4,880,918; U.S. Pat. No. 5,049,372; U.S. Pat. No. 5,070,877; U.S. Pat. No. 5,104,859; Daval et al., "Physiological and Pharmacological Properties of Adenosine Therapeutic Implications," *Life Sciences* 49:1435–1453 (1991); Dubyak et al., Eds., *Biological Actions of Extracellular ATP*, Annals of the New York Academy of Sciences v. 603, New York, N.Y. Academy of Sciences (1990); Imai et al., Eds., *Role of Adenosine and Adenine Nucleotides in the Biological System. Metabolism, Release, Transport. Receptors, Transduction Mechanisms and Biological Actions*, Amsterdam, Elsevier (1991); Ribeiro, Ed., *Adenosine Receptors in the Nervous System*, London, Taylor & Francis (1989); Williams, Ed., *Adenosine and Adenosine Receptors*, Clifton, N.J. The Humana Press (1990); Tsuchida et al., "Pretreatment with the adenosine $A_1$ selective agonist, 2-chloro-N6-cyclopentyladenosine (CCPA), causes a sustained limitation of infarct size in rabbits," *Cardiovascular Research*, 27:652–66 (1993); Fukunaga et al., "Hypotensive effects of adenosine and adenosine triphosphate compared with sodium nitroprusside," *Anesthesia and Analgesia* 61:273–278 (1982); Fukunaga et al., "Effects of intravenously administered adenosine and ATP on halothane MAC and its reversal by aminophylline in rabbits," *Anesthesiology*, 71:A260 (1989); Drury et al. "The physiological activity of adenine compounds with special reference to their action upon the mammalian heart", *Journal of Physiology* (London) 68:213–37 (1929); Olsson et al. "Cardiovascular purinoceptors," *Physiological Reviews*, 70:761–809 (1990); Downey et al., Ed. "Spotlight on the cardioprotective properties of adenosine", *Cardiovascular Research*, v. 27, No. 1 whole issue (1993); Rudolphi et al., Neuroprotective role of adenosine in cerebral ischemia," *Trends in Pharmacological Sciences*, 13:439–45 (1992); and Williams, "Purinergic pharmaceuticals for the 1990s," *Nucleosides & Nucleotides*, 10:1087–99 (1991); U.S. Pat. No. 5,082,829; 5,132,291; 5,187,162; 5,200,525; 5,236,908; Homeister et al., "Combined adenosine and lidocaine administration limits myocardial reperfusion injury," *Circulation* 82:595–608 (1990); Mullane K, "Acadesine: the prototype adenosine regulating agent for reducing myocardial ischaemic injury," *Cardiovascular research* 27:43–7 (1993); Van Belle H, "nucleoside transport inhibition: a therapeutic approach to cardioprotection via adenosine?," *Cardiovascular Research* 27:68–76 (1993); all of which are incorporated by reference. Perhaps the greatest problem with attempts to utilize purine compounds as therapeutic agents is due to the undesired and often fatal side effects associated with providing sufficient amounts of a purine compound to a patient to induce a desired effect. For example, it has been well documented that adenosine plays a key role in the endogenous defenses of the brain against the damaging effects of ischemia. Moreover, adenosine has been reported to protect the heart when given both prior to ischemia and at reperfusion; however, intravenous administration of adenosine or even an $A_1$ selective agonist has been shown to cause profound hypotension ($A_1$ represents one of the purported adenosine receptors in mammalian systems). In another example, anesthesia is induced in a mammal by administering large amounts of adenosine or ATP; however, anesthetically effective dosages can be fatal to the recipient if extreme care is not followed in administering same (e.g., titration of adenosine in response to accurate monitoring of patient vital signs) or if a counteracting agent is not provided promptly in response to dangerous patient vital function levels. Even with prior or subsequent provision of agents to counteract certain undesired effects of administering the large dosages of adenosine, or an adenosine analog, sufficient to induce anesthesia, dangerous variations in vital functions can result. This "pendulum effect" on patient physiological processes, which is reflected in large changes in patient vital signs, such as but not limited to blood pressure, heart rate, and respiration, discourages the therapeutic use of purine compounds.

Therefore, there is a need for purine compositions comprising a purine compound which can be more easily and safely administered in a sufficient amount to induce a desired effect without inducing an undesired effect which is usually associated with administering the same amount of purine compound alone. Most prior attempts to counteract the undesired effects of administering a purine compound have involved the use of receptor specific antagonists. Furthermore, it was believed that, due to the dissimilar structure and function of the purine compounds with respect to the agents which counteract certain undesired effects of administering the purine compounds, that the purine compounds and counteracting agents could not be simultaneously used or mixed together in-vitro and still be safely administered for therapeutic purposes.

SUMMARY OF THE INVENTION

Briefly, and in general terms, the present invention provides for purine compositions and methods of administering the purine compositions, in which a synergistic and unexpected beneficial result is obtained by combining a purine compound with a counteractive agent, wherein the pendulum effect or radical variation in certain patient vital functions have been greatly reduced, and high dosages of a purine compound, previously believed to cause a dangerous or fatal undesired effect, can be safely administered to induce a desired effect while reducing an undesired effect.

Thus, the present invention is directed to purine compositions, and methods of administering the purine compositions. The purine composition preferably comprise a purine compound and a counteractive agent, in which the purine compound induces a desired effect and an undesired effect when administered in an effective amount to a mammal without administering the counteractive agent, and the counteractive agent, when combined with the purine compound prior to administration of the effective amount of the purine compound, reduces an undesired effect of the effective amount of the purine compound upon administration of the combination to a mammal.

In a preferred embodiment, purine compounds capable of inducing a desired effect, such as but not limited to central nervous system inhibition, neuroprotection, autonomic nervous system modulation or inhibition, cardiac protection, and respiratory protection, analgesia/anesthesia but which also induce an undesired effect, such as but not limited to severe hypotension and cardiodepression, are combined in vitro with a counteractive agent which reduces an undesired effect while permitting the purine compound to induce a desired effect when the mixture is administered. Compositions in accordance with the present invention can be formulated batchwise long periods of time in advance of administration, or, for example, can be mixed in a suitable fitting attached to an IV set just prior to passage into a patient, or the components of the composition can be simultaneously administered. In a preferred embodiment, the purine compound is selected from the group consisting of adenosine, adenosine analogs, phosphorylated adenosine, and phosphorylated adenosine analogs, and is combined with a counteractive agent. In a preferred embodiment, the counteractive agent is a catecholamine, such as but not limited to epinephrine, norepinephrine, dopamine, dobutamine, and phenylephrine.

In another aspect, a purine composition is formed by combining a purine compound, a counteractive agent, and a purine compound potentiator and/or a CNS depressant. The potentiator may be a compound which inhibits uptake of the purine compound, or a compound which interferes with the ability of endogenous enzymes to metabolize or otherwise degrade the purine compound, or a compound which enhances adenosine release or a combination of any of them. The potentiator may be compounds such as but not limited to an adenosine uptake (transport) inhibitor (e.g., dipyridamole); an adenosine deaminase inhibitor (e.g., deoxycoformycin, and erythro-9-(2-hydroxy-3-nonyl) adenine; a precursor (e.g. AICA riboside.); a CNS depressant (e.g., a benzodiazepine, such as diazepam, midazolam, and flumazenil, an opioid, such as morphine, fentanyl, and sufentanil, or a barbiturate, such as thiopental, and methohexital, etomidate, propofol); an adrenergic $\alpha_2$- agonist (e.g., clonidine, and dexmedetomidine); or a non-steroidal anti-inflammatory drug (e.g. aspirin, ibuprofen, ketorolac).

In another aspect, the present invention has led to the discovery that the multiple effects of the present composition can be used in concert with other drugs producing synergistic effects of their combined activity.

The present composition can be used as a carrier of other drugs such as antibiotics, antipyretics, anti-viral, anti-cancer, anti-toxin, chemotherapeutic agents, potassium channel openers, and the like. The effects of the present composition as a blood flow regulator/modulator will selectively target pathological tissues/organs and will enhance the desirable effects of other drugs as well. For example, the affirmative and desirable effects of opioids, benzodiazepines and the like, can be enhanced while the side effects and/or undesirable effects of such drugs can be counteracted. Thus the combined use of various drugs as in the present composition can act as catalysts. For example, by the methods and compositions according to the invention, the respiratory depression effects caused by the opioids and the benzodiazepines can be counteracted, while the salutary effects such as the analgesic and sedative effects can be potentiated.

In another aspect, the present invention has also led to the discovery that surprisingly large dosages of a catecholamine compound, previously thought sufficient to induce dangerous or fatal side effects, can be administered by combining the catecholamine compound with a counteractive agent prior to administration, wherein the catecholamine compound can induce a desired effect upon administration in an effective amount, while the counteractive agent reduces an undesired effect or effects upon administration of the combination to a mammal. In a preferred embodiment, the catecholamine is combined with a purine compound to form a catecholamine composition capable of inducing a desired catecholamine effect while reducing one or more undesired effects which would result if the catecholamine had been administered without first being combined with the purine compound.

In another aspect, it has been surprisingly discovered that high dosages of a purine compound or a catecholamine compound can now be safely administered to a mammal by mixing the appropriate ratio of purine compound or catecholamine compound with a counteracting agent. For example, higher dosages of a purine compound and a catecholamine compound can be safely administered to a mammal than previously thought possible by combining the purine compound and the catecholamine compound in predetermined ratios prior to administration. Appropriate ratios of purine compound or catecholamine compound to counteracting agent in pharmaceutical compositions according to the present invention can be readily determined by one of ordinary skill in the art by performing a few routine tests, which involve the monitoring of vital signs of interest (e.g., blood pressure, heart rate, respiration) while administering varying ratios of purine compound or catecholamine compound to counteracting agent, and at varying compound dosages.

By way of a nonlimiting example, initially administering low dosages (e.g., dosages known to be safe) of a purine compound combined with a counteracting agent in varying ratios will enable determination of the appropriate ratio of purine compound to counteractive agent which begin to induce a desired effect while reducing an undesired effect; dosages can then be increased and the ratio of purine compound to counteracting agent adjusted to optimize the desired effect achieved while minimizing an undesired effect. In a preferred embodiment, a purine composition, comprising between about 1 part by weight norepinephrine combined with about 25 to 2,000 parts by weight adenosine can be administered to a mammal to induce a desired effect while reducing an undesired effect, wherein the undesired effect would occur to a much greater degree were it not for the presence of the norepinephrine in the composition. Other nonlimiting examples of preferred inventive compositions include compositions comprising 1 part epinephrine combined with between about 50 and about 4,000 parts by weight adenosine, compositions comprising one part by weight phenylephrine combined with about 10 to about 200 parts by weight adenosine, and compositions comprising one part by weight dopamine combined with about two to about fifty parts by weight adenosine. The preceding compositions can have varying dosages of adenosine.

Catecholamine compositions in accordance with the present invention can be formed by combining a catecholamine compound with a counteracting agent and determining the appropriate dosages and ratios for obtaining the desired effect while minimizing undesired effects.

The same principle can be applied for the use of adenosine analogs that have much longer effects. For this, longer acting catecholamines can be combined in the composition, or a separate, infusion of counteractive catecholamines can be administered in one or more stages, preferably in a continuous infusion commencing at some time following infusion of an initial mixture of an adenosine analog and catecholamine. In addition, the composition can be formulated with an additive that can make it absorbable from gastrointestinal tracts/organs, and be easily ingested (taken orally, enterally).

One of ordinary skill in the art will recognize that the ratios of catecholamine compound or purine compound to counteracting agent can be adjusted depending on patient physiology, vital signs, and the therapeutic purpose (e.g., a hypotensive and/or bradycardic patient will require less adenosine to induce normotension, while a hypertensive and/or tachycardiac patient will require more adenosine to induce the same effect). Likewise, dosage will depend on the desired effect and patient physiopathology. The compositions of the present invention may be formed in combination with pharmaceutically acceptable carriers, and stored in accordance with standard procedures and precautions for medicinal compositions. The present invention pioneers the use of purine compounds to efficaciously activate purine receptors for therapeutic purposes.

The present invention pioneers the therapeutic use of high dosages of purine compounds and catecholamine compounds for a wide variety of uses, as well as pioneers the use of new and useful purine and catecholamine compositions formed by combining a purine compound or a catecholamine compound with a counteracting agent. For example, purine compositions prepared in accordance with the present invention can be administered in an amount effective to induce anesthesia and analgesia faster and/or more safely than present anesthetic methods. Further, administration of purine compounds according to the present invention has demonstrated CNS inhibitory effects, and the effects of modulation of the autonomic nervous system and modulation of circulation, respiration as well as homeostatic metabolism. It may be used in cardioprotection, neuroprotection, pulmonary protection, metabolic homeostasis preservation, sedation, anethesia, antipyretic, antihypertensive treatment, and prevention and/or treatment of ischemia/hypoxia.

The invention is further described and illustrated by the following detailed description and nonlimiting examples.

DESCRIPTION OF THE DRAWINGS

FIGS. 2(a)-(b) are blood pressure (mmHg) tracings from a rabbit administered bolus injections of adenosine alone, norepinephrine alone, or a combination of adenosine and norepinephrine;

FIG. 4(a) is a blood pressure tracing over time which illustrates the effects of administering bolus injections of ATP and norepinephrine;

FIG. 4(b) is a blood pressure tracing over time which illustrates the reduction in the blood pressure pendulum effect when high dosages of ATP combined with norepinephrine are administered from a pre-mixed solution;

DETAILED DESCRIPTION OF THE PREFERRED EMBODIMENTS

Figure 1A:
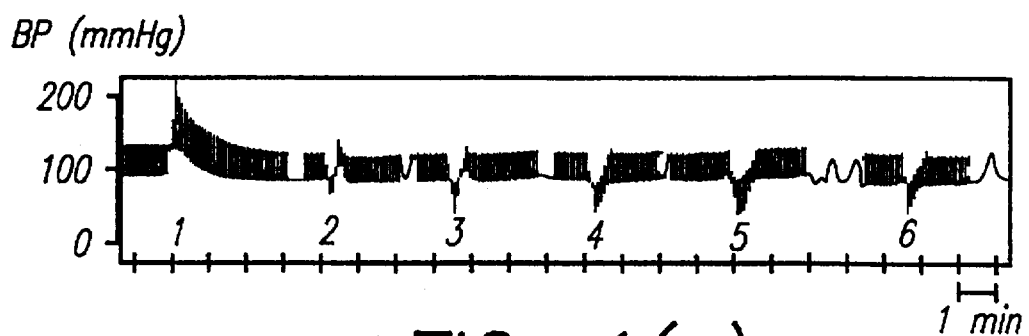
FIGS. 1(a)-(d) are blood pressure (in mmHg) recordings over time following administration of bolus injections of a catecholamine alone, adenosine alone, or varying combinations of adenosine with a catecholamine.

It has been surprisingly discovered that, despite the dissimilar structure and function of purine compounds and their counteracting agents, that they have sufficiently similar pharmacokinetics to be used simultaneously or to be combined together in vitro and administered, so that certain of the undesired effects of administering purine compounds alone can be offset by the coadministered counteracting agents. Further, it has been surprisingly discovered that the in-vitro combination of the purine compounds with counteracting agents does not result in an adverse reaction in-vitro, or in-vivo following administration, and that surprisingly improved results can be achieved by administering a mixture of a purine compound with a counteractive agent. In fact, it is amazing that such unforseen synergistic effects of two potent and antagonistic substances when used simultaneously or combined together in vitro could have such enhanced and significant biological effects. For the purposes of this disclosure, a purine compound is defined as a compound including the purine functionality (by way of nonlimiting example, adenosine), a purine analog, or a purine receptor agonist, which has at least one desired effect and at least one undesired effect upon administration to a mammal in an amount sufficient to induce a desired effect ("purine effect"). A catecholamine compound is defined herein as a catecholamine (by way of nonlimiting example, norepinephrine), a catecholamine analog, or a catecholamine receptor agonist having at least one desired effect ("catecholamine effect") and at least one undesired effect upon administration to a mammal of an amount sufficient to induce a desired effect. A counteracting agent is defined as an agent which is capable of reducing an undesired effect caused by administration to a mammal of an effective amount of a purine compound or a catecholamine compound. As used hereinafter, the term "AC" refers to a combination or simultaneous administration of adenosine, adenosine analogs, phosphorylated adenosine, or phosphorylated adenosine analogs, and catecholamine, and "ACB" is the combinational use of AC and benzodiazepine.

As shown in the figures for purposes of illustration and as discussed above, the present invention has tremendous benefits to medicine, and pioneers new purinergic therapies and adrenergic therapies. This is partly because larger doses of purine compounds and catecholamine compounds than were previously thought possible can now be safely administered to a mammal to induce a desired effect while reducing at least one undesired effect previously associated with administering such a dosage. As is illustrated by the blood pressure, BP, tracings in FIG. 1(a), provision of a purine compound, such as adenosine, or a catecholamine compound, such as norepinephrine, alone, induces severe alterations in patient vital functions. It is noted that, although blood pressure is primarily used in this disclosure to demonstrate this phenomenon, other patient vital functions can be monitored as well to illustrate the beneficial effects of the present invention. For example, in addition to blood pressure, other patient vital functions which can be monitored include but are not limited to electrocardiogram, EKG, respiratory rate, RR (breaths per minute), heart rate, HR (beats per minute, BPM), body temperature, and blood gas data: $PaCO_2$ and $PaO_2$ for respiratory parameters, pH, and base excess (BE) for metabolic parameters.

The present invention enables the therapeutic use of purine and catecholamine compounds by reducing the severe side effects associated with administering a sufficient dosage of a purine compound or a catecholamine compound to induce a desired effect. The attenuation or dampening of undesired radical alterations in certain patient vital functions by administration of compositions prepared in accordance with the present invention is made clear by the following nonlimiting examples.

As a nonlimiting example of how one of ordinary skill in the art would determine the appropriate ratio of a purine compound combined with a counteracting agent in a composition formed in accordance with the present invention, the following steps can be followed: A desired effect of administering a purine compound can be achieved by administering a sufficient amount of the purine compound to a mammal to induce the desired effect. For example, adenosine can be administered to a patient to induce an analgesic/anesthetic effect provided a sufficient amount of adenosine is administered to the patient. However, administering a dosage of adenosine to a mammal sufficient to induce analgesia/anesthesia will also induce severe hypotension and cardio-depression, which can be monitored by blood pressure recording devices and heart rate (EKG) monitors. The degree of hypotension and cardio-depression can be sufficient to cause irreversible damage to patient vital organs, or may even induce death. Therefore, it is necessary to first determine the appropriate ratio of adenosine to counteracting agent in the purine compound composition to be administered to the patient. In order to do this, the patient vital functions of interest, for example, the heart rate and blood pressure, can be monitored prior to and during administration of compositions containing varying ratios of the purine compound to the counteracting agent (e.g., adenosine to catecholamine ratio).

Initially, only small dosages of the purine compound which are known not to cause dangerous side effects should be administered in combination with a counteracting agent which is also provided at a dosage sufficiently small that it is known to cause no adverse side effects. The ratios of the purine compound to the counteracting agent can then be titrated to attenuate radical fluctuations in the vital function of interest. Thereafter, the combined dosages of purine compound and counteracting agent can be gradually increased, with the ratio of the purine compound combined with counteracting agent adjusted to optimize patient vital functions of interest.

Because of the similarity of physiological response to purine compounds and catecholamine compounds in humans and in rabbits, rabbits provide an ideal source of information on the appropriate ratios of purine compound or catecholamine compound to counteracting agent in compositions to be administered to a human. Those of ordinary skill in the art will immediately recognize that dosages and ratios may vary from patient to patient depending upon the type of therapy desired and on the particular patient. As with the administration of any drug, those of ordinary skill in the art should follow normal procedures for minimizing the risk of adverse reactions when supplying compositions in accordance with the present invention to a patient receiving other drugs or therapies. See Gilman et al., Eds., Goodman and Gilman's. *The Pharmacological Basis of Therapeutics*, 9th ed., New York, Pergamon Press (1990); and Katzung, Ed., *Basic and Clinical Pharmacology*, 5th Ed., Norwalk, Appleton & Lange (1992).

Compositions of the present invention may be administered with pharmaceutically acceptable carriers, and may be combined with a potentiator, which may increase or prolong the beneficial effects of the purine or catecholamine compound. In the event of contraindications, dosages may be adjusted by a physician administering compositions of the present invention, or additional amounts of a purine compound, a catecholamine compound, and/or a counteracting agent may be administered.

Some patients have reported discomfort, such as headaches, flushing, and angina-like chest pain following administration of purine compounds, such as adenosine. In order to minimize this discomfort, a central nervous system, CNS, depressant may be administered to the patient first, or may be combined with a purine composition or a catecholamine composition prepared in accordance with the present invention. Suitable CNS depressants include but are not limited to benzodiazepines, opioids, barbiturates, and propofol.

In a preferred embodiment, adenosine compounds can be combined with an adenosine potentiator, such as but not limited to an adenosine uptake inhibitor (e.g., dipyridamole, dilazep, benzodiazepine), and/or an adenosine deaminase inhibitor (e.g., 2'deoxycoformycin, and erythro-9-(2-hydroxy-3-nonyl)adenine. Thus, in an alternative embodiment, a purine compound or catecholamine compound combined with a counteracting agent is also combined with a purine compound or catecholamine compound potentiator. In yet another embodiment, a purine compound or a catecholamine compound combined with a counteracting agent are also combined with a CNS depressant. In another embodiment, a purine compound is combined with a counteracting agent, a CNS depressant, and a purine compound potentiator. In yet another embodiment, a catecholamine compound is combined with a counteracting agent, a CNS depressant, and a catecholamine compound potentiator.

The protective effects of administering a purine compound, such as adenosine, combined with a counteracting agent, such as a catecholamine, have also been clearly demonstrated by administration of a purine composition prepared in accordance with the present invention to a mammal suffering from severe respiratory depression and seizure activity caused by high dose opioids like fentanyl. Administration of a purine composition in accordance with the present invention also protects mammals from noxious stimulation by inducing both sedative and potent analgesic effects, while protecting the cardiovascular and metabolic functions which are usually affected by stressful conditions, such as excessively high plasma catecholamine levels and pain.

Figure 10:
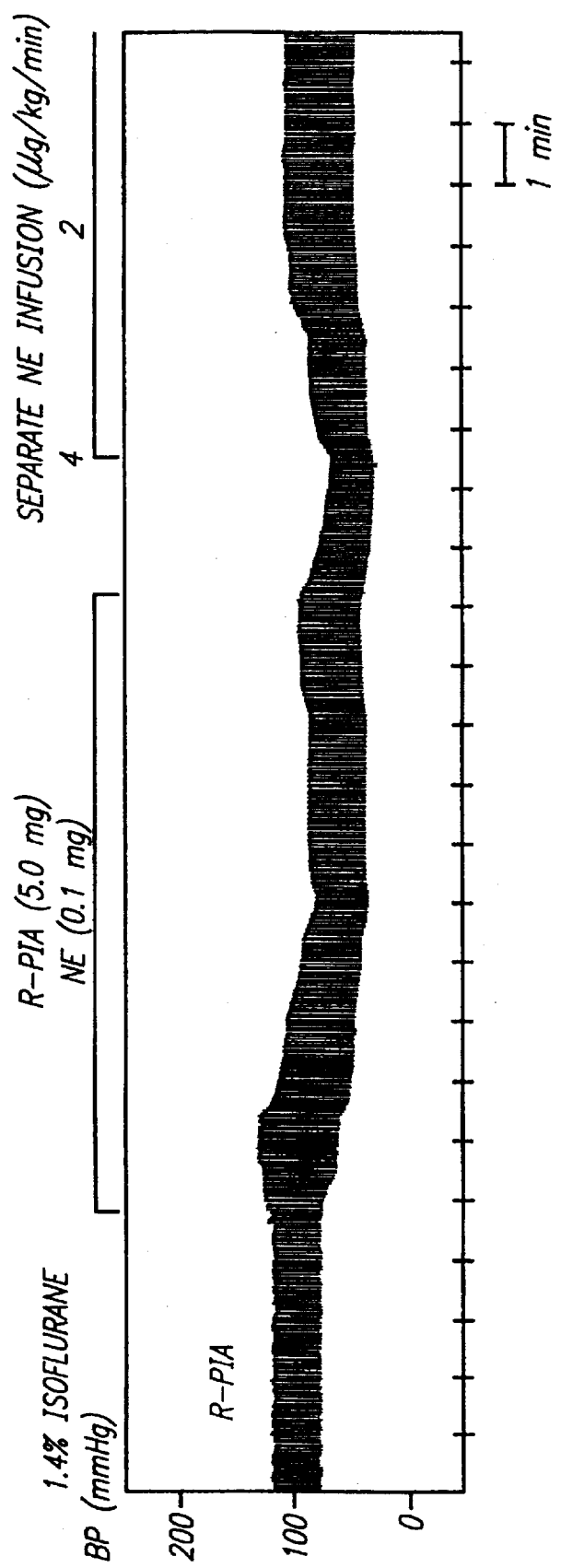
FIG. 10 is a blood pressure recording over time following an initial administration of a longer lasting adenosine analog, R-PIA, along with norepinephrine, and subsequent administration of norepinephrine, illustrating a method of administering longer lasting adenosine analogs with catecholamine according to the invention.
Figure 11:
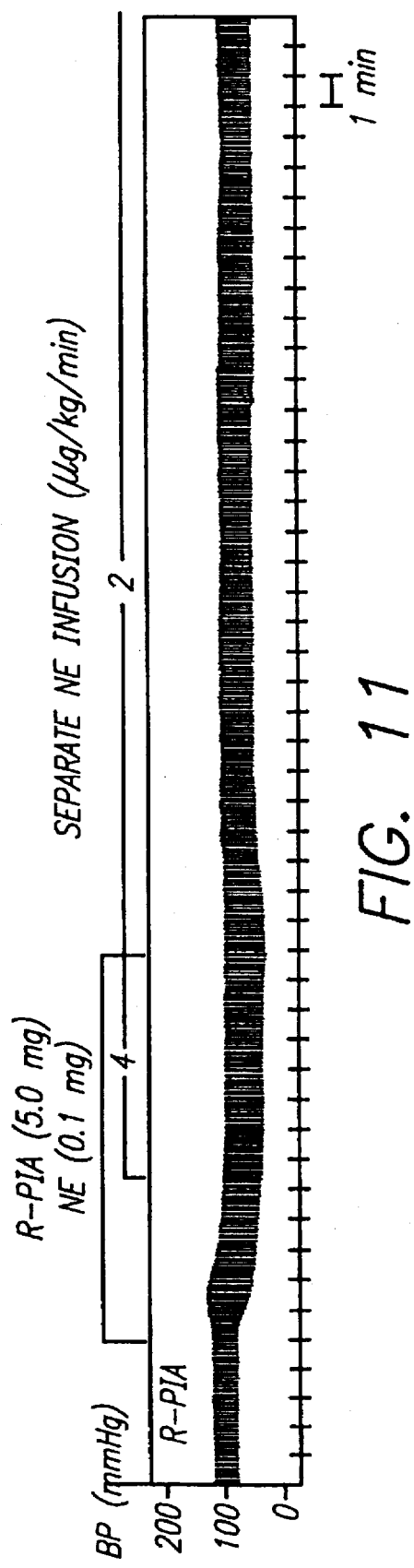
FIG. 11 is a blood pressure recording over time following an initial administration of a longer lasting adenosine analog, R-PIA, along with norepinephrine, and subsequent administration of norepinephrine, illustrating another method of administering longer lasting adenosine analogs with catecholamine according to the invention.
Figure 12:
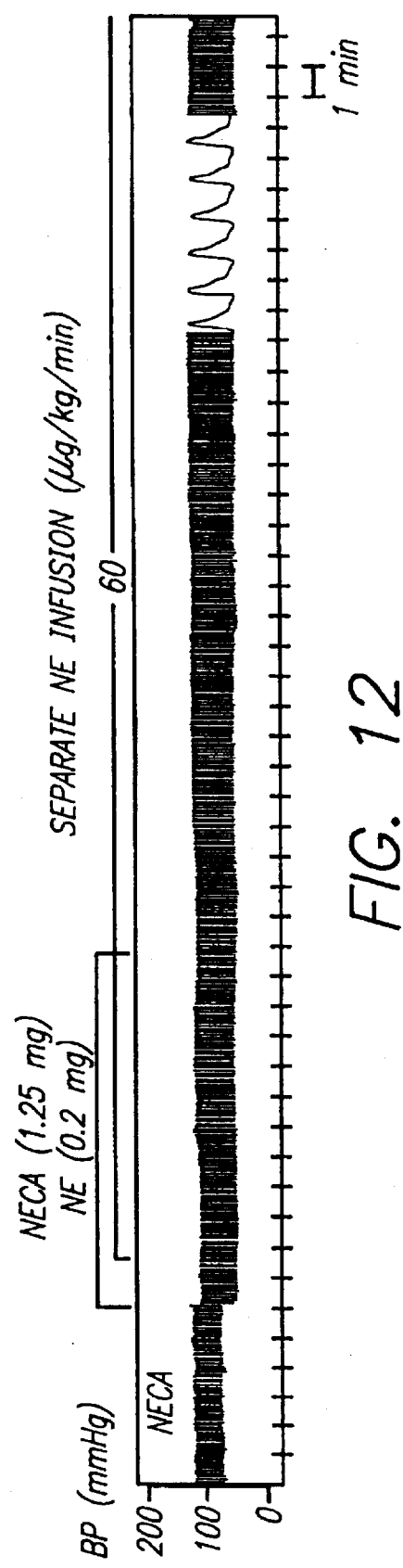
FIG. 12 is a blood pressure recording over time following an initial administration of a longer lasting adenosine analog, NECA, along with norepinephrine, and subsequent administration of norepinephrine, illustrating another method of administering longer lasting adenosine analogs with catecholamine according to the invention.

With reference to FIGS. 10–12, the method of the invention for administering a purine compound in combination with a catecholamine counteractive agent can also further comprise the administration of one or more separate infusions of additional catecholamine counteractive agent following the initial infusion of purine compound and catecholamine counteractive agent. Adenosine analogs that can be used in the compositions and method of the invention include, but are not limited to, 5'-N-ethylcarboxamidoadenosine (NECA), R(-)$N^6$-(2-phenylisopropyl) adenosine (R-PIA), 2-chloroadenoine (2-CADO), $N^6$-cyclopentyladenosine (CPA), and $N^6$-cyclohexyladenosine (CHA), for example. Such adenosine analogs can have longer lasting effects in the body than adenosine, and in particular can have longer lasting effects in the body than catecholamines typically co-administered with adenosine, such as norepinephrine, for example, so that the co-administration of catecholamine with an adenosine analog can further include judicious administration of at least one separate infusion of a selected catecholamine as the effects of a selected adenosine analog continue even beyond administration is stopped. The additional infusion of the selected catecholamine counteractive agent following the initial infusion of the mixture is preferably administered by a separate, continuous infusion of the catecholamine, and in one preferred embodiment, the additional infusion of catecholamine is administered in stages of progressively reduced dosages over time, as the selected adenosine analog is gradually metabolized.

The beneficial effects of administering the purine compositions and catecholamine compositions of the present invention to mammals are further illustrated by the following nonlimiting examples.

EXAMPLE 1

Hemodynamic Effects of Intravenous Administration of a Combination of Adenosine-Catecholamine (AC)

Materials and Methods

Drugs: Adenosine and ATP (adenosine 5'-triphosphate, disodium salt) were obtained from Kyowa Hakko Kogyo Co., Tokyo, Japan, and dissolved in standard saline solution. Norepinephrine bitartrate injection (LEVOPHED) was obtained from Winthrop Pharmaceuticals, and midazolam hydrochloride was obtained from Roche Laboratories.

Unmedicated, healthy New Zealand white rabbits (male and female), weighing 2.5–2.7 Kg were studied. Rabbits were chosen because they are an excellent indicator of how these drugs and methods will work in humans. Anesthesia was initially induced with halothane 3–4% in oxygen using a face mask, and the animals were allowed to breath spontaneously. A tracheostomy was performed on each rabbit, and a 3.5 F (French size) cuffed pediatric endotracheal tube was inserted into the trachea. The inhaled concentration of halothane was then lowered, and maintained with 1.5–2% halothane in 10.0% oxygen during the preparation. Local infiltration with lidocaine (1% solution) was done when a tracheostomy and femoral cut down were performed. An ear marginal vein and a central artery were cannulated with 22 and 24 gauge plastic catheters for drug and fluids administration and for blood sampling. After intravenous access was established, lactated Ringer's solution was started at 5 ml/kg/hr for fluid maintenance. The femoral artery was cannulated with a polyethylene catheter (PE 120) which was placed with its tip in the mid-thoracic aorta to measure central arterial blood pressure. The catheter was well secured and the skin was closed. The heart rate was continuously monitored via percutaneous leads (II) electrocardiograph (EKG), connected to a Hewlett Packard 78304A polygraph and recorded on a Hewlett Packard 78172A recorder. Body temperature was continuously monitored by means of a rectal probe, and maintained between 38.5°–39.5° C. with the aid of a heating lamp.

After completion of the experimental preparation, halothane was discontinued and the rabbits were placed in a sling in a natural, physiological posture which allowed the animal's head and legs freedom to move. After complete recovery from the halothane anesthesia, the following control measurements were taken from the unanesthetized animals: systolic blood pressure (SBP), diastolic blood pressure (DBP), mean arterial pressure (MAP), Respiratory Rate (RR), Heart Rate (HR), ECG, Body Temperature (BT), arterial blood gases: $PaCO_2$, $PaO_2$, pH, and base excess (BE). Blood gases were measured with a Radiometer ABL 30 blood gas analyzer.

Results and Conclusions

In order to determine the optimal concentration ratio of the components of the adenosine-catecholamine, AC, composition, various concentrations of an adenosine compound (A) and a catecholamine (C) alone were separately injected, and then mixtures of adenosine with catecholamine having varying ratios of adenosine to catecholamine were tested in the in vivo experimental animal model. The results of these experiments are shown in FIGS. 1 and 2 which illustrate the effects on blood pressure (mmHg) over time from administering a purine compound or catecholamine alone, or from administering varying compositions of a purine compound combined with a catecholamine.

Figure 1B:
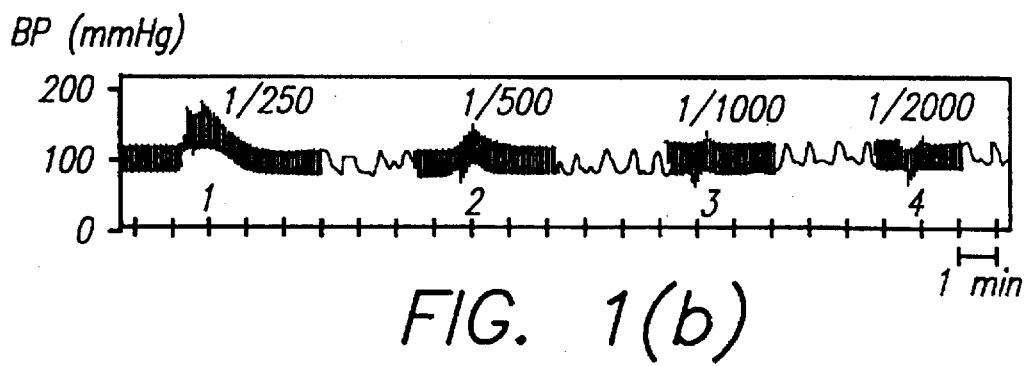
Figure 1C:
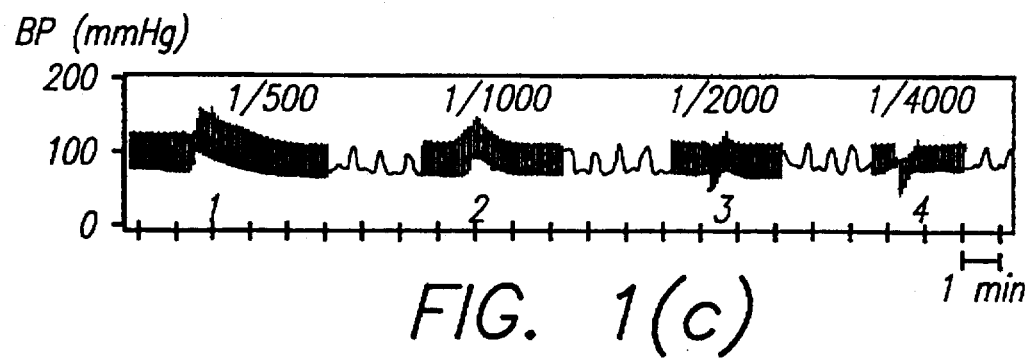
Figure 1D:
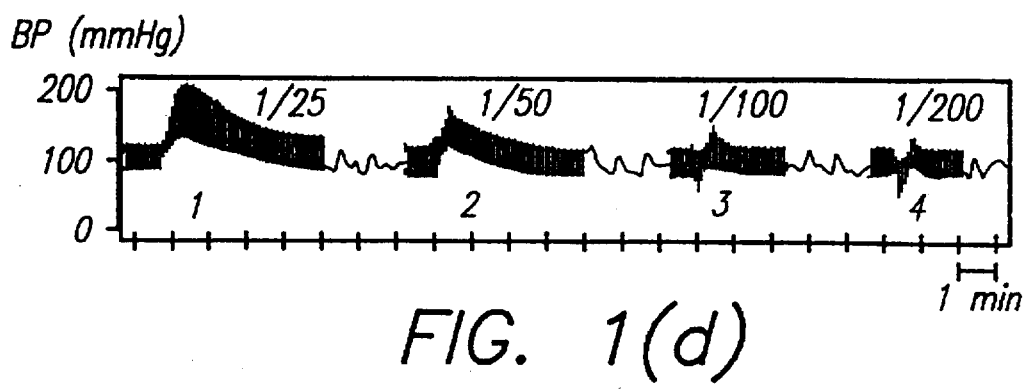

The above process was repeated several times for each animal, and with various combinations of adenosine and a catecholamine respectively, as illustrated in FIGS. 1(a)–(d). FIG. 1(a) has six separate tracings which result from administration of purine and catecholamine compounds as follows: FIG. 1(a), tracing (a)1: 20 µg norepinephrine; (a)2: 5 mg adenosine; (a)3: 10 mg adenosine; (a)4: 20 mg adenosine; (a)5: 40 mg adenosine; and (a)6: 20 mg adenosine. FIG. 1(b) illustrates four tracings which result from administration of the following compositions formed from 20 mg adenosine combined with varying amounts of a catecholamine: (b)1: 1 part norepinephrine mixed with 250 parts adenosine (i.e., 20 mg adenosine combined with 0.08 mg norepinephrine); (b)2: 1 part norepinephrine mixed with 500 parts adenosine; (b)3: 1 part norepinephrine mixed with 1,000 parts adenosine; (b)4: 1 part norepinephrine mixed with 2,000 parts adenosine. FIG. 1(c) illustrates four tracings which result from administration of the following compositions formed from 20 mg adenosine combined with varying amounts of a catecholamine: (c)1: 1 part epinephrine mixed with 500 parts adenosine; (c)2: 1 part epinephrine mixed with 1,000 parts adenosine; (c)3: 1 part epinephrine mixed with 2,000 parts adenosine; (c)4: 1 part epinephrine mixed with 4,000 parts adenosine. FIG. 1(d) illustrates four tracings which result from administration of the following compositions formed from 20 mg adenosine combined with varying amounts of a catecholamine: (d)1: 1 part phenylephrine mixed with 25 parts adenosine; (d)2: 1 part phenylephrine mixed with 50 parts adenosine; (d)3: 1 part phenylephrine mixed with 100 parts adenosine; (d)4: 1 part phenylephrine mixed with 200 parts adenosine. Parts are given as parts by weight.

The tracings in FIG. 2(a) illustrate the effects on blood pressure from administration of the following: (a)1: 10 mg/kg adenosine; (a)2: a mixture of 10 mg/kg adenosine with 0.01 mg/kg norepinephrine (ratio of 1000/1 adenosine to norepinephrine); (a)3: 0.01 mg/kg norepinephrine. FIG. 2(b) is a blood pressure tracing which results from administration of a mixture of 100 mg/kg adenosine with 0.1 mg/kg norepinephrine (ratio of 1000/1 adenosine to norepinephrine).

Once the adequate concentration ratio was determined for each animal, a large dose of the AC mixture solution was injected to test the blood pressure responses during the administration (FIG. 2(b)). A series of nine experiments were carried out in the rabbit model to estimate and determine the AC concentration ratio that showed minimal blood pressure changes, and to determine the effectiveness of the AC compositions having varying dosages and ratios of adenosine compounds to catecholamines. The cardio-respiratory vital signs of the rabbits were continuously monitored during and after administration of the AC mixture. Table 1 summarizes the effective concentration ratio of adenosine and 4 different catecholamines in mixtures administered to 9 animals which demonstrated minimum variations in blood pressure.

TABLE 1

Determination of Concentration Ratios of Adenosine (A) and Catecholamines (C) Which Demonstrated Minimum Blood Pressure Fluctuations. (Parts by Weight Adenosine to 1 Part by Weight of Designated Catecholamine.)

Catecholamine/Adenosine

| Rabbit # | Norepinephrine | Epinephrine | Dopamine | Phenylephrine |
|---|---|---|---|---|
| 1 | 1/1000 | 1/2000 | 1/5.0 | 1/200 |
| 2 | 2000 | 4000 | 5.0 | 200 |
| 3 | 1000 | 2000 | 5.0 | 100 |
| 4 | 500 | 1000 | 2.5 | 50 |
| 5 | 1000 | 2000 | 5.0 | 100 |
| 6 | 500 | 1000 | 2.5 | 50 |
| 7 | 500 | 1000 | 2.5 | 50 |
| 8 | 1000 | 2000 | 5.0 | 100 |
| 9 | 1000 | 2000 | 5.0 | 100 |
| Mean ± SD | 944 ± 464 | 1889 ± 928 | 4.2 ± 1.3 | 106 ± 59 |
| C/A Ratio | 1/944 | 1/1889 | 1/4.2 | 1/106 |

Through these in vivo tests, the concentration ratios which cause minimum fluctuations in blood pressure can be determined for each combination of purine compound and counteracting agent. FIG. 2(a) shows the blood pressure changes when adenosine (ADO), norepinephrine (NE) and their combination (AC) is injected. The recordings demonstrate that administration of adenosine only (10 mg/kg, Tracing 1) causes profound hypotension. Likewise norepinephrine only (0.01 mg/kg, Tracing 3) causes excessive hypertension. However, the fluctuations (up and down) in the blood pressure are minimal after injection of the same dosages of adenosine (10 mg/kg) and norepinephrine (0.01 mg/kg) combined in-vitro prior to administration (ratio of 1000/1 adenosine to norepinephrine). The blood pressure recording in FIG. 2b illustrates the stability of a mammal's blood pressure during administration of a large dose of AC (ADO: 100 mg/kg, and NE: 0.1 mg/kg, ratio of 1000/1 adenosine to norepinephrine) manually administered over a duration of about 10 minutes.

Table 2 summarizes the hemodynamic, respiratory and metabolic data obtained before and after intravenous injection of an ACB (Adenosine-Catecholamine-Benzodiazepine) combination in spontaneously breathing rabbits (the benzodiazepine added in this example is midazolam, which acts as a CNS depressant as well as an adenosine uptake inhibitor).

TABLE 2

Cardiovascular, Respiratory and Metabolic Data Before and After Intravenous Injection of Large Doses of ACB in Spontaneously Breathing Rabbits

| | Pre-injection (5 min before) | Post-injection (5 min after) | Δ Change | P Value |
|---|---|---|---|---|
| Blood Pressure (mmHg) | | | | |
| Systolic (SBP) | 116 ± 7 | 113 ± 7 | −3 | NS |
| Diastolic (DBP) | 85 ± 6 | 76 ± 11 | −9 | NS |
| Mean (MAP) | 95 ± 6 | 90 ± 9 | −5 | NS |
| Heart Rate (HR) | | | | |
| (beats/min) | 240 ± 31 | 239 ± 37 | −1 | NS |
| Arterial Blood Gases | | | | |
| pH | 7.40 ± 0.09 | 7.33 ± 0.08 | −0.07 | 0.015 |
| $PCO_2$ (mmHg) | 28 ± 4 | 32 ± 10 | +4 | NS |
| $PO_2$ (mmHg) | 583 ± 21 | 574 ± 19 | −9 | NS |
| BE (mEQ/L) | −5.4 ± 5.1 | −8.0 ± 4.2 | −2.6 | 0.005 |
| Respiratory Rate (RR) | | | | |
| (breath/min) | 71 ± 22 | 71 ± 30 | 0 | NS |
| Body Temperature (BT) | | | | |
| °C. | 38.5 ± 0.05 | 38.2 ± 0.6 | −0.3 | NS |

(ACB (Adenosine/Catecholamine/Benzodiazepine) in 0.9% saline); Adenosine (117 ± 41 mg/kg); Norepinephrine (0.106 ± 0.05 mg/kg); Midazolam (1.05 ± 0.43 mg/kg); N = 9; Mean ± SD.

As can be appreciated from the data in Table 2, the administration of huge doses of adenosine: 117±41 mg/kg, norepinephrine: 0.106±0.051 mg/kg, and midazolam: 1.05±0.43 mg/kg caused minimal changes in all of the hemodynamic, respiratory and metabolic parameters of the subjects. These data and the recordings in FIG. 2(a) and 2(b) clearly demonstrate that large doses of adenosine and norepinephrine, combined in vitro in accordance with the invention, can be safely administered in order to induce a desired effect (e.g., analgesia, sedation, etc . . . ) without causing deleterious cardiovascular, respiratory, or metabolic conditions.

The model system represented in the above example is designed to test the BP responses of the healthy, normotensive animal. However, the present method or principle is expected to be applicable to humans as well, particularly in view of the known effects of administering dosages of purine compounds and catecholamine compounds to humans.

In addition, administration of large dosages of adenosine or ATP combined with the appropriate ratio of a catecholamine can be injected to more quickly induce a desired effect, e.g., anesthesia, than by slowly infusing low dosages of adenosine or ATP alone. It has also been surprisingly discovered that, while the vasodilating effects of anesthetically effective amounts of purine compounds, such as adenosine or ATP, last about as long as the purine compounds remain at the effective concentrations in the blood plasma, certain effects, such as analgesia, last for much longer time periods. Thus, a patient administered a purine composition in accordance with the present invention to induce anesthesia may not require any, or as much, pain reducing drugs following surgery. Further, administration of purine compositions formed in accordance with the present invention reduces the release of endogenous catecholamines in response to trauma (such as that induced in surgery). Thus, administration of a purine composition of the present invention is believed to reduce the need for an anesthesiologist to administer drugs to counteract endogenous catecholamine induced effects during surgery.

EXAMPLE 2

Central Nervous System (CNS) Inhibition by Administration of ACB (Adenosine-Catecholamine-Benzodiazepine)

The broad depressant effects on the CNS of exogenously administered adenosine, adenosine analogs and adenine nucleotides are well documented; those related to antinociception, reduction in sensing pain, have been reviewed extensively. It is believed that a major problem of the hypotensive effects of adenosine may complicate the systemic routes of administration to a point where therapeutic considerations are limited. Therefore, the present study was undertaken to find out whether intravenous administration of ACB could attain CNS inhibitory actions, such as sedative and analgesic effects, without causing severe hypotension.

Materials and Methods

Unmedicated, healthy New Zealand white rabbits were studied. The animals were prepared as in Example 1. The sedative and antinociceptive effects were tested following the methodology described in Example 1 of copending U.S. patent application Ser. No. 08/437,280, which is a continuation of Ser. No. 08/083,214 which is useful for testing and screening the analgesic and anesthetic effects of adenosine compounds.

A pair of stimulating needle electrodes were placed at the base of the shaved tail of each rabbit. After the animals were placed in a sling and had complete recovery from anesthesia, electrical current (noxious stimuli) was delivered through a nerve stimulator (Grass S48 Stimulator); in addition, conventional tail clamping (a standard test for anesthetic effects) was done. The control values were measured and recorded. No other drug was used, and the animals were allowed to breath 100% $O_2$ spontaneously without mechanical ventilatory assistance. Blood pressure changes were continuously monitored and recorded. Neurobehavioral responses, including degree of sedation, arousal responses (eye opening and head lifting), and antinociceptive responses (purposeful escape movement) were carefully observed and recorded throughout the experiment.

A large dose of ACB (adenosine: 100 mg/kg, norepinephrine: 0.1 mg/kg, midazolam: 1 mg/kg) was slowly injected into a peripheral ear vein over a duration of about 10 minutes. After 20 minutes, three types of electrical stimulation, 2 Hz, 5 Hz, and 50 Hz, were delivered to the rabbits. By changing the voltage intensity, two behavioral responses were recorded for each test: a) head lift (HL), an arousal response shown by opening the eyes and lifting the head (hypnotic/sedative index); and b) purposeful escape movement, as in trying to run, or escape movement (EM) away from the noxious stimulus (analgesic index). Noxious stimuli were delivered every 30 minutes, and the sedative and nociceptive thresholds were recorded. Also, the blood pressure (BP), the heart rate (HR), EKG, respiratory rate, blood gases ($PaCO_2$ and $PaO_2$), and blood pH and base excess (BE) were recorded.

Results and Conclusions

Figure 3:
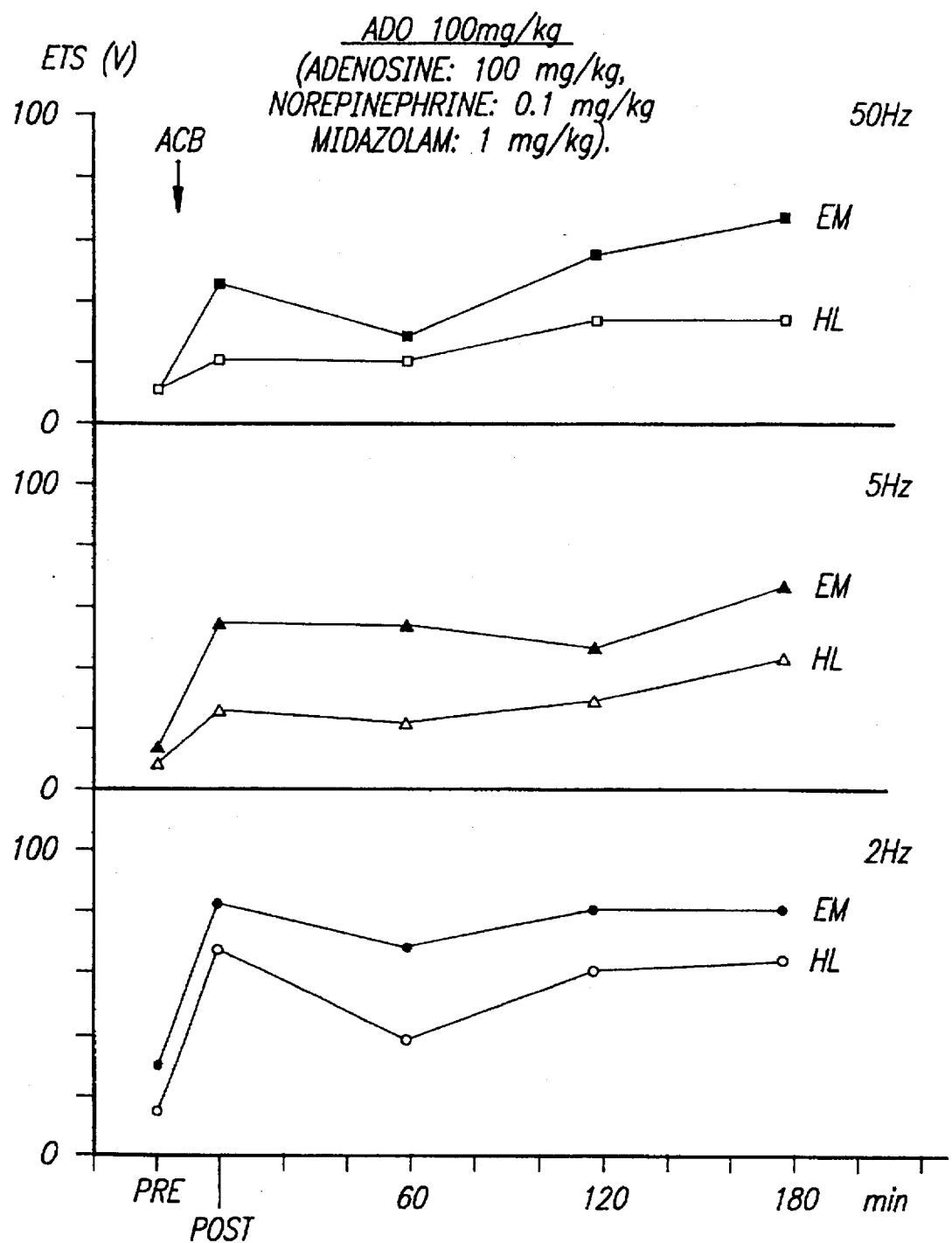
FIG. 3 illustrates sedative and antinociceptive thresholds in response to electrical tail stimulation, ETS, before and after administration of a mixture of adenosine, catecholamine, and benzodiazepine.

The administration of ACB caused minimal blood pressure changes similar to the BP changes illustrated in FIG. 2(b) where the same dosage of 100 mg/kg adenosine and 0.1 mg/kg norepinephrine was administered. In addition, the animals were all well sedated, which is supported by the elevation of the sedative (HL) responses to electrical stimulation. The antinociceptive (EM) as well as the sedative (HL) thresholds were consistently elevated in all three types of electrical stimulation after administration of ACB. The animals also did not respond to tail clamping, indicating a potent CNS mediated depressant effect. Furthermore, such sedative and analgesic activity was sustained for at least three hours after administration, as is illustrated in FIG. 3. At all three ETS levels (2 Hz, 5 Hz & 50 Hz), the thresholds for both escape movement and head lift were consistently elevated following administration of the ACB composition.

FIG. 4(a) is a blood pressure tracing (mm Hg) over time, that shows, moving left to right, the effects of administering bolus injections of 0.1 mg/kg adenosine triphosphate (ATP), 1.0 mg/kg ATP, 10 mg/kg ATP, and 10 µg/kg norepinephrine, (NE). FIG. 4(b) shows the blood pressure, BP, recording obtained during continuous infusion of a very large dose of AC (ATP:200 mg/kg, and norepinephrine:0.67 mg/kg) which was initiated 10 minutes after administration of 2 mg/kg diazepam (a sedative). The mixture of ATP and catecholamine is also referred to as AC. A total dosage of 200 mg/kg ATP and 0.67 mg/kg norepinephrine is supplied via a continuous infusion of AC (ratio of ATP to NE of 300/1). The continuous infusion of AC was initiated at ATP 100 µg/kg/min, then increased to 3200 µg/kg/min where it was maintained for about 30 minutes, and thereafter the dosage was decreased gradually toward the end of the infusion. This further shows that large doses of ATP and norepinephrine combined in vitro in accordance with the invention can be administered while maintaining stable blood pressure at variable rates of infusion for a long time.

The above BP recording illustrated in FIG. 4(a) demonstrates the BP swings during administration of ATP and norepinephrine alone. Notice that 0.1, 1.0, and 10 mg/kg of ATP caused hypotensive effects in a dose dependent manner. Likewise, a small dose of norepinephrine (0.01 mg/kg) caused excessive elevation of the BP. However, FIG. 4(b) illustrates the reduction in the blood pressure pendulum effect which would otherwise occur from administration of ATP or NE separately, and the BP changes are minimal when the AC combination is administered, despite the huge dosage of ATP and norepinephrine.

Figure 5:
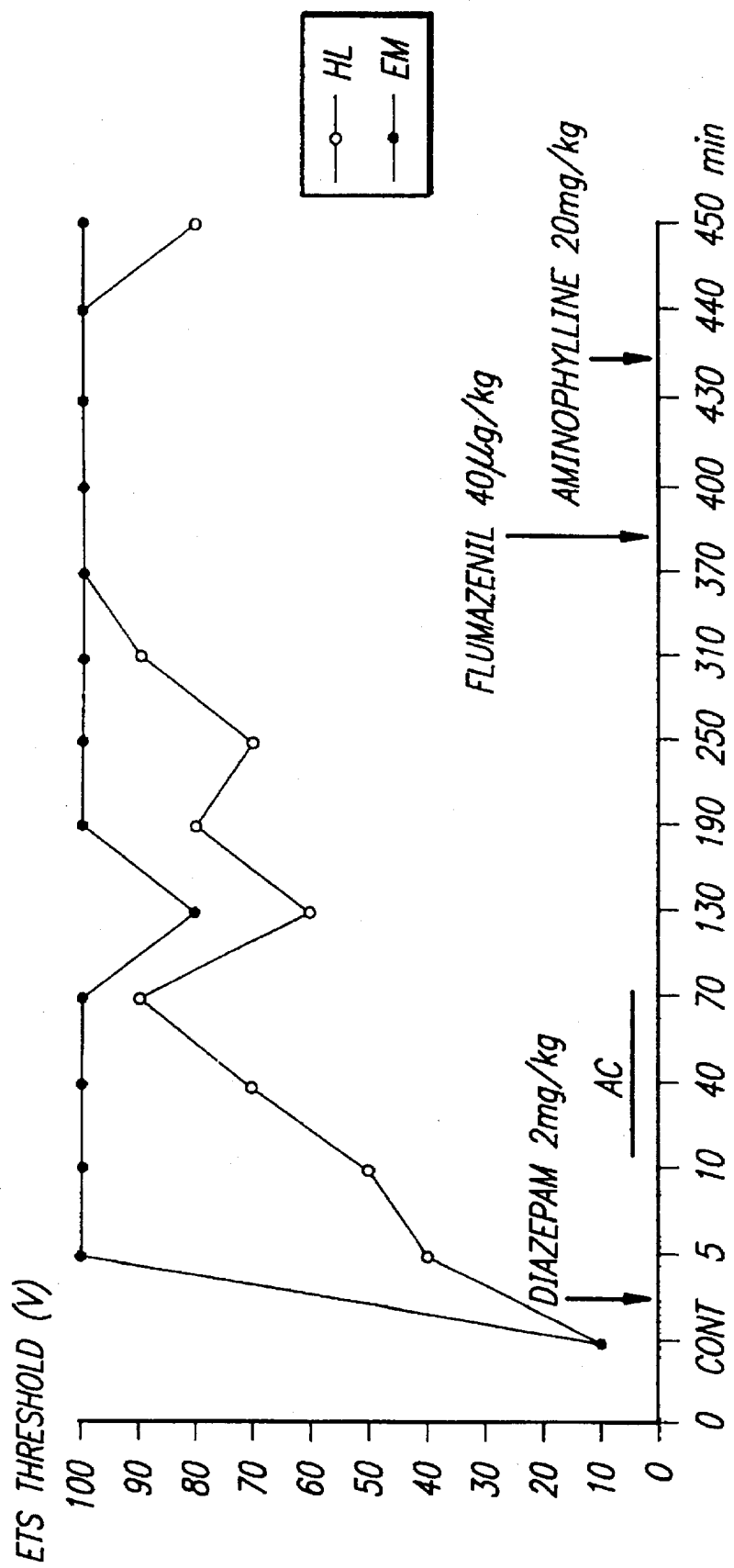
FIG. 5 illustrates the duration of the sedative and analgesic effects after administration of diazepam (2 mg/kg) and AC (ATP: 200 mg/kg combined with NE:0.8 mg/kg)

FIG. 5 illustrates that following the administration of diazepam (2 mg/kg) and AC (ATP: 200 mg/kg combined with NE: 0.67 mg/kg), analgesic effects can be sustained for at least 5 hours. In FIG. 5, the vertical axis represents sedative and analgesic thresholds in response to electrical tail stimulation (ETS) in voltage (V). The horizontal axis represents time in minutes and the time at which drugs were administered. AC was administered as a continuous infusion over 60 minutes. FIG. 5 illustrates that sedative and analgesic effects are sustained for over five hours after administration of AC, despite administration of flumazenil, a diazepam antagonist. Aminophylline did not completely antagonize the escape movement (EM) antinociceptive response but lowered the head lift (HL) arousal response. The cardiovascular, respiratory and metabolic changes are shown in Table 3.

a suspended sling. The animals were divided into 2 groups. Each group consisted of 4 animals: The rabbits were pretreated with (a) saline or (b) AC (combination of ATP:100 mg/kg and NE: 0.2 mg/kg). A high dose of fentanyl: 100 µg/kg (Janssen Pharmaceutica, N.J.) was administered twice. The first injection was 10 minutes after the pretreatment with saline or AC, and the second dose was administered after 40 minutes. Cardiovascular and blood gas data were recorded right after the pretreatment drug was administered, and then at 5, 10, 20 and 30 minutes following administration of fentanyl. Also, the neuro-behavioral and the nociceptive thresholds were assessed as in Example 2 by tail clamping and electrical tail stimulation.

TABLE 3

Cardiovascular, Respiratory and Metabolic Data Before, During and After AC Administration

|  | Control | Diazepam 10 min After | During AC Infusion | Post AC Administration | | | | | |
| --- | --- | --- | --- | --- | --- | --- | --- | --- | --- |
|  |  |  |  | 30 min | 1 hr | 2 hrs | 3 hrs | 4 hrs | 5 hrs |
| BP (mmHg) | 89 | 92 | 77 | 106 | 106 | 105 | 102 | 99 | 107 |
| HR (beats/min) | 214 | 236 | 226 | 198 | 211 | 208 | 200 | 206 | 234 |
| PaCO$_2$ (mmHg) | 34.6 | 31.0 | 32.8 | 21.2 | 29.4 | 31.2 | 32.1 | 34.7 | 32.4 |
| PaO$_2$ (mmHg) | 548 | 490 | 551 | 517 | 502 | 549 | 508 | 498 | 435 |
| BE | −6.7 | −6.4 | −1.1 | −5.8 | −1.0 | −0.2 | 0.4 | 1.2 | 2.0 |
| RR (breath/min) | 40 | 50 | 180 | 140 | 160 | 130 | 90 | 90 | 100 |
| BT (°C.) | 36.9 | 36.9 | 36.6 | 36.4 | 37.4 | 37.8 | 37.8 | 37.7 | 38.0 |

AC (ATP: 200 mg/kg, Norepinephrine: 0.67 mg/kg); Diazepam: 2 mg/kg; BP: Blood Pressure; HR: Heart Rate; RR: Respiratory Rate; BT: Body Temperature.

The above studies demonstrate that AC, or AC combined with a sedative, can be effectively administered without the side effects of physical discomfort and/or hypotension while achieving CNS inhibitory effects of sedation and analgesia, and without respiratory depression or metabolic deterioration.

EXAMPLE 3

Protection from High-Dose Opioid-Induced Cardio-Respiratory and Metabolic Disturbances with Pretreatment by Administration of AC to Spontaneously Breathing Rabbits Administration of high doses of opioids has been the most frequently used anesthetic technique for open-heart surgery. However, the use of high doses of synthetic opioids (e.g., fentanyl, sufentanil, alfentanil) has been reported to cause central seizure activity, and to increase both sympathetic and parasympathetic (vagal) activities with excessively elevated plasma catecholamine levels. In addition, opioids may cause profound respiratory depression and serious signs of cardiopulmonary dysfunctions, including ischemic EKG abnormalities, hemorrhagic pulmonary congestion and left ventricular failure of the heart. In contrast, exogenously administered adenosine has been reported to stimulate ventilation and has been found to have potent analgesic effects. We hypothesized that, if sufficiently large dosages of AC (e.g., adenosine-norepinephrine) could be administered safely, this could protect mammals from the above mentioned deleterious effects of high opioid dosages. Therefore, the present study investigated whether intravenous administration of AC could protect against the cardio-pulmonary and metabolic disturbances caused by the administration of high doses of fentanyl.

Materials and Methods

The experimental preparation was done as in Example 1. Tracheotomized and cannulated rabbits were each placed in

Results and Conclusion

Figure 6A:
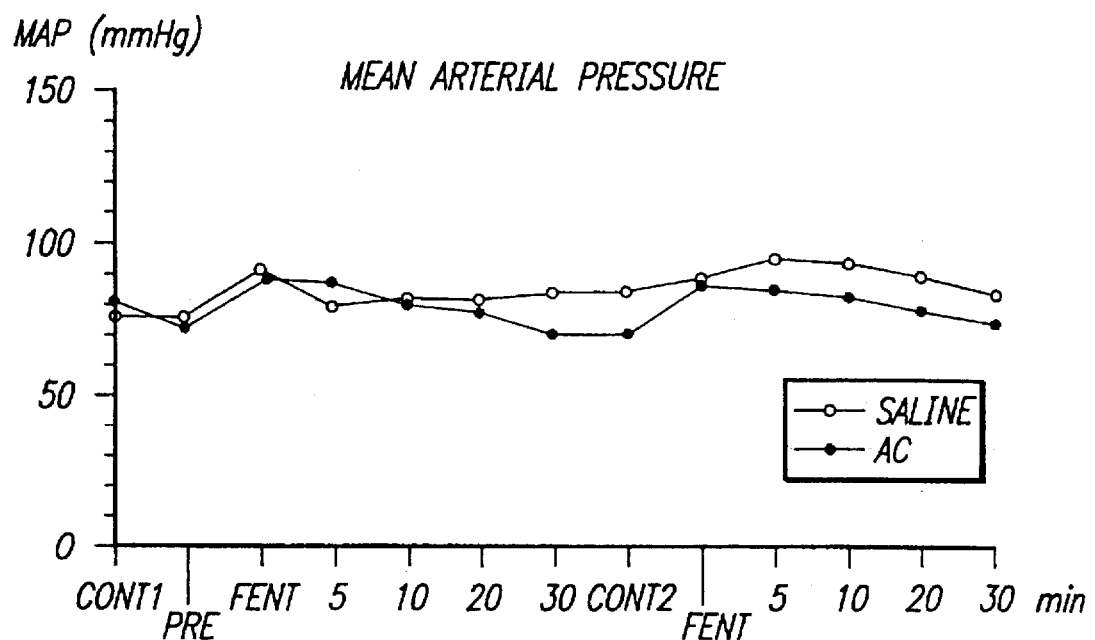
FIGS. 6(a)-(j) illustrate the cardiorespiratory and metabolic assessment following high dose-fentanyl administration in two groups pretreated with: a) saline, or b) AC (ATP:100 mg/kg and NE:0.2 mg/kg)

Data are summarized in FIGS. 6(a)–(h). Fent (fentanyl: 100 µg/kg) was first injected 10 minutes after pretreatment with either pretreatment a or b, and a second injection of Fent was given at 40 minutes. Cont1 and Cont2 represent control data before injection of drugs. FIG. 6(a), provides MAP: mean arterial pressure; 6(b) provides HR: heart rate; 6(c) provides PaCO$_2$: arterial carbon dioxide tension; 6(d) provides PaO$_2$: arterial oxygen tension. Notice that administration of fentanyl produced severe respiratory depression which resulted in a progressive increase in PaCO$_2$ and a decrease in PaO$_2$, as can be seen in 6(c) and (d). When hypercapnia became severe after the second administration of fentanyl, the AC pretreated group suddenly increased respiratory rate as seen in 6(e) resulting in a decrease of PaCO$_2$ as seen in 6(c) and an increase in PaO$_2$ as seen in 6(d), while the metabolic parameters of pH as seen in 6(g) and BE: base excess as seen in 6(h) were ameliorated.

Figure 6B:
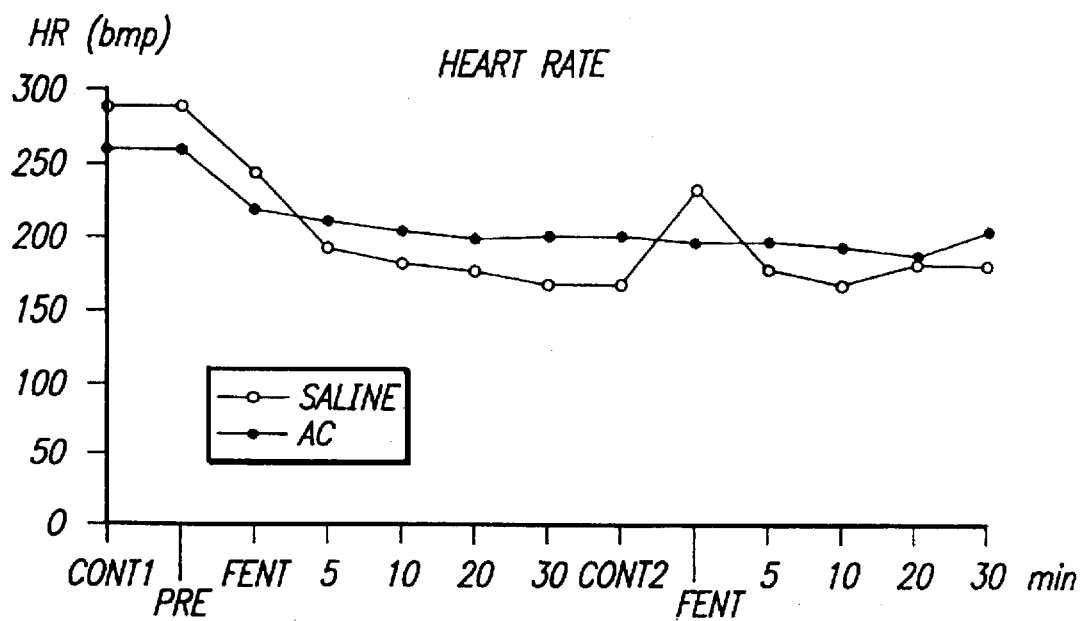
Figure 6C:
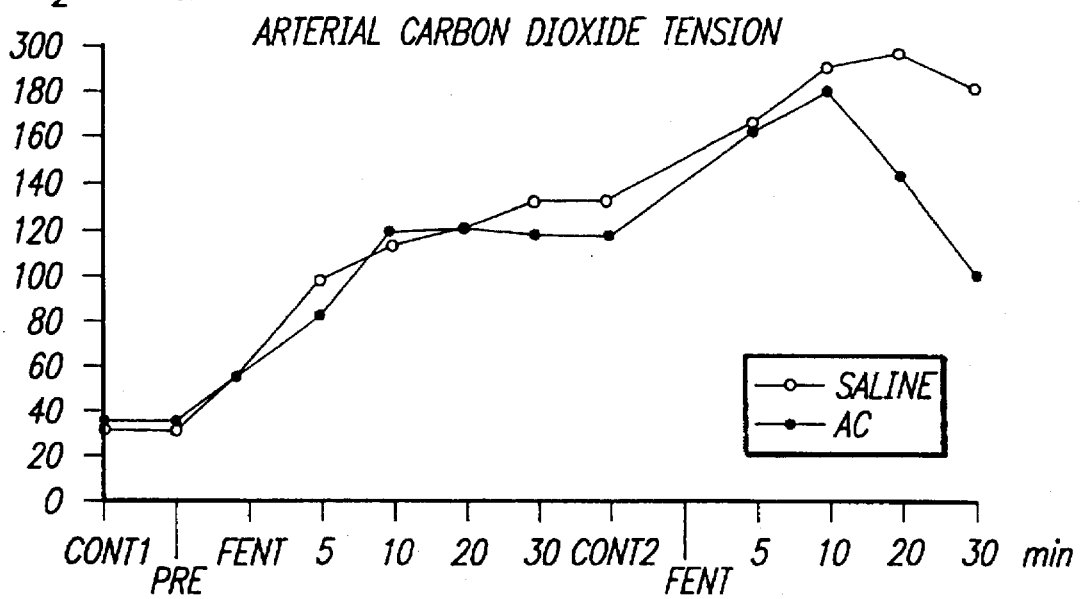
Figure 6D:
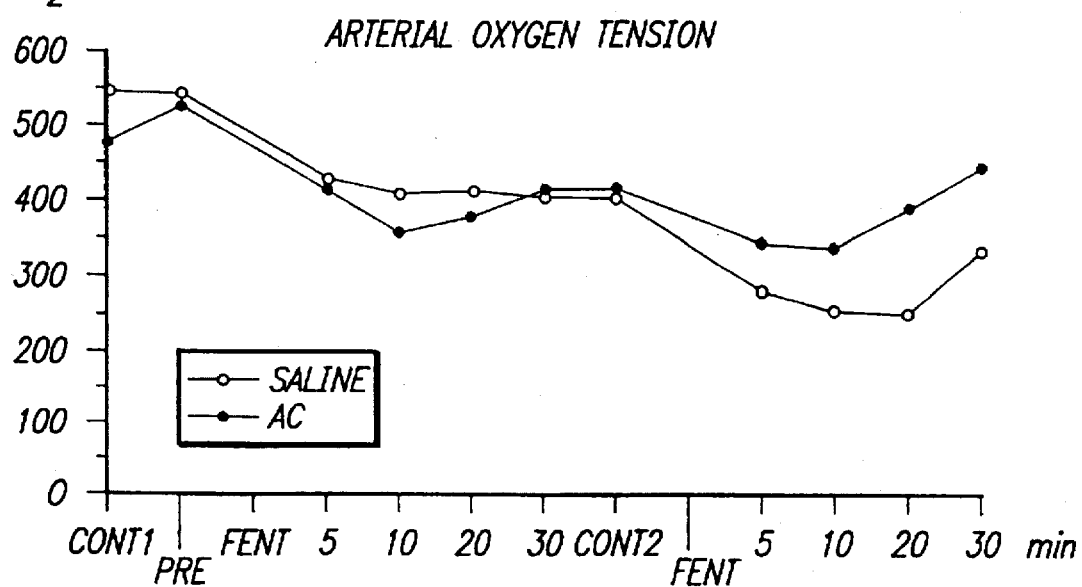
Figure 6E:
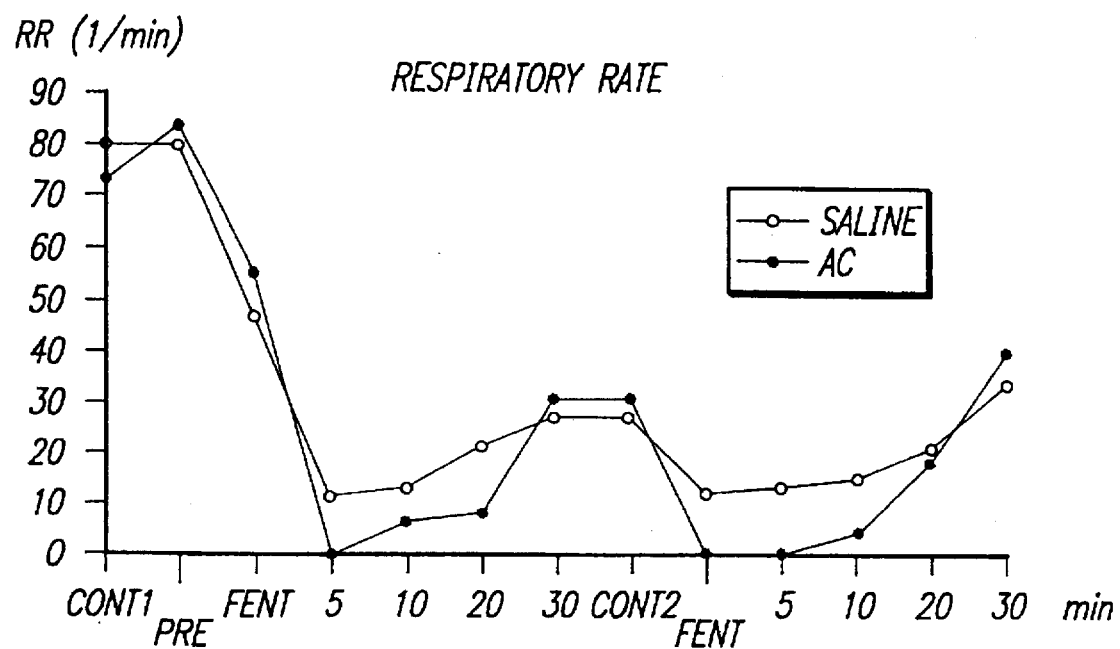
Figure 6F:
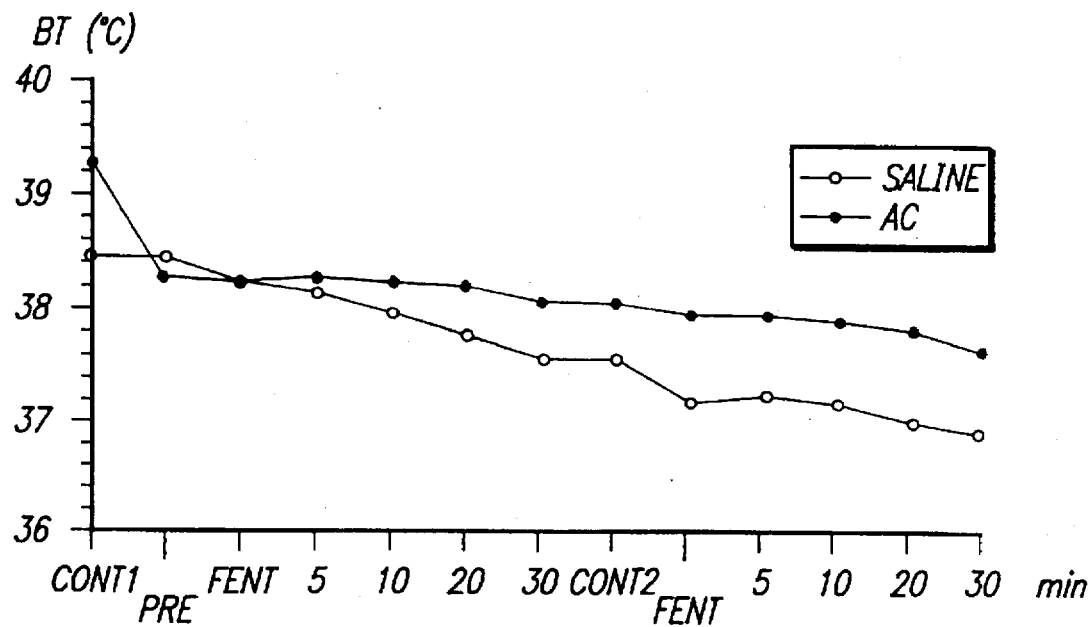
Figure 6G:
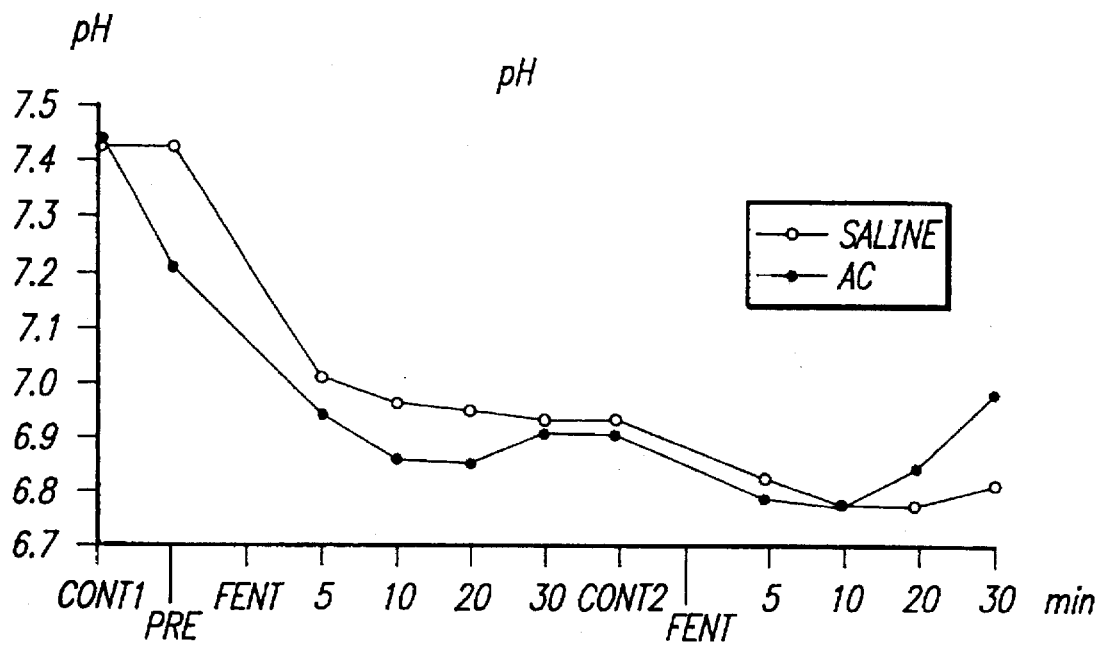
Figure 6H:
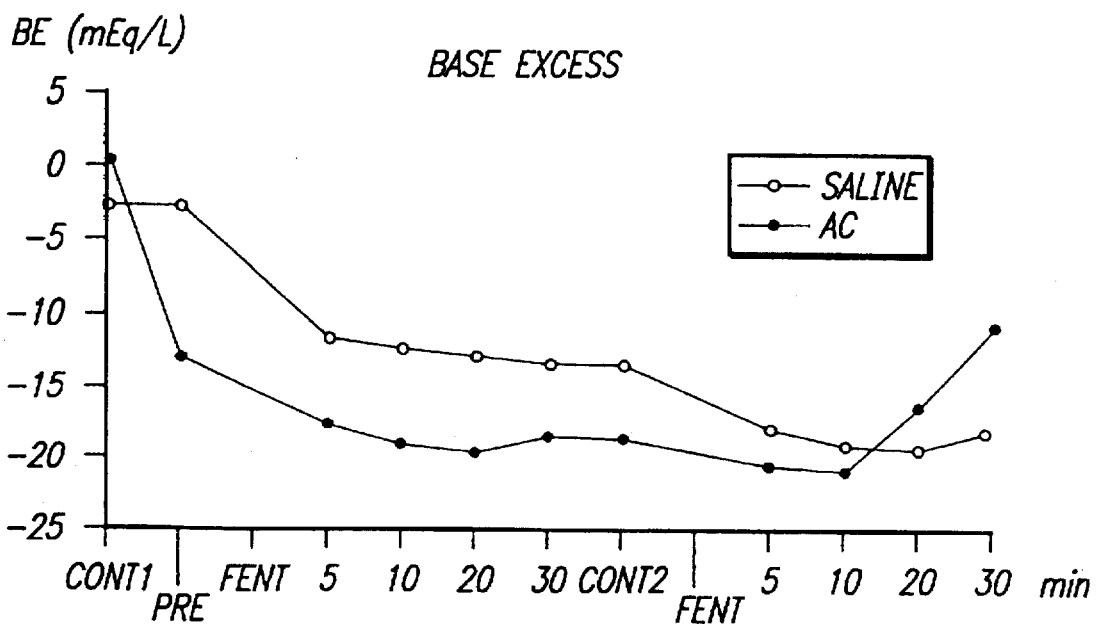
Figure 6I:
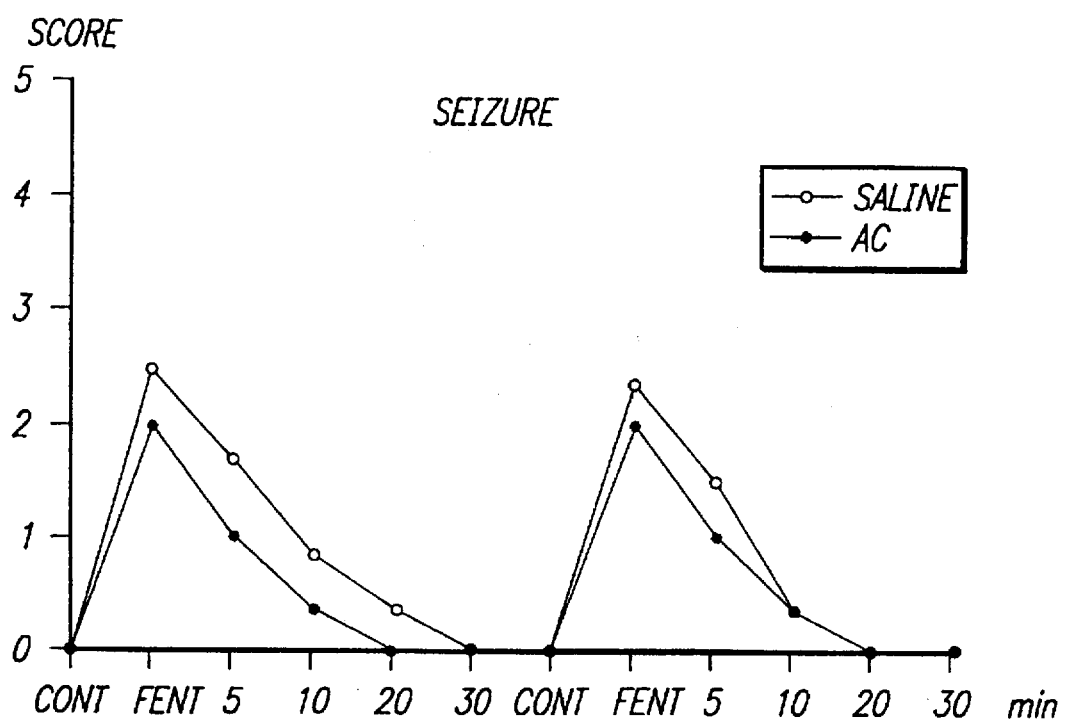
Figure 6J:
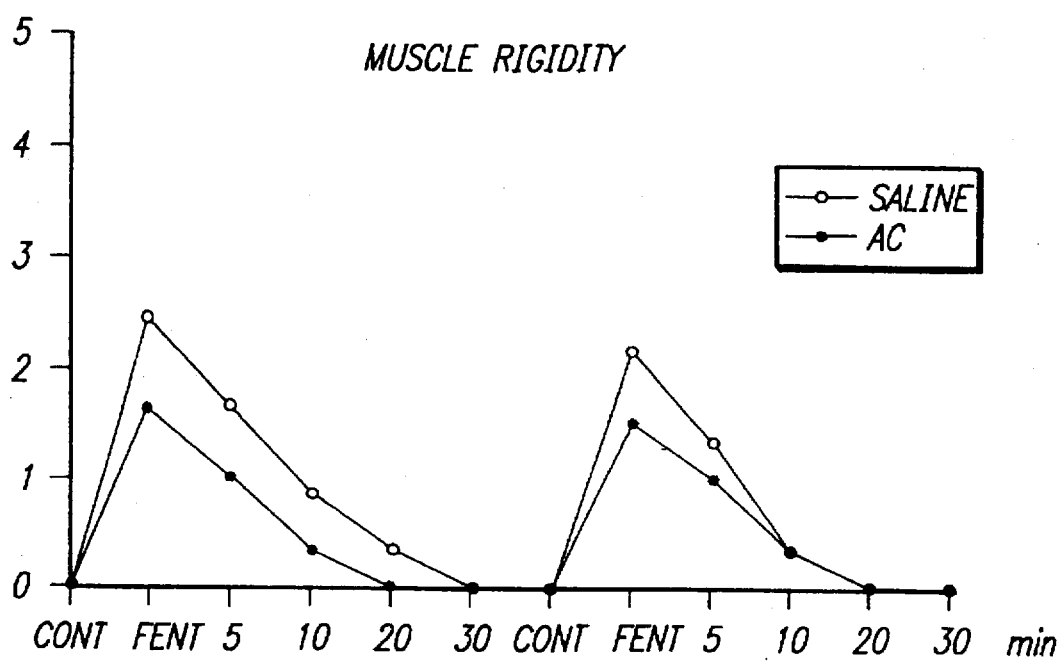

As can be appreciated from FIGS. 6(a)–(b), the fluctuations in the blood pressure and heart rate due to the fentanyl injections are attenuated in the animals administered the AC composition compared to those administered saline. The incidence of seizure activity and the degree of skeletal muscle rigidity were less in the AC group than in the saline group (see FIG. 6(i)–(j)). The threshold responses to noxious stimulation in the form of electrical stimulation and tail clamping were also higher in the AC group. These results demonstrate the beneficial effects rendered by the pretreatment with the AC composition by protecting the patients from the cardio-respiratory and metabolic disturbances caused by administering a high dosage of an opioid (e.g., fentanyl). In addition, AC rendered neuroprotection from seizure activities.

EXAMPLE 4

Cardiopulmonary Protective Effects of the AC (Adenosine/Catecholamine) Composition The protective and homeostatic actions of adenosine are well accepted. Extensive studies on the involvement of endogenous and exogenous adenosine in myocardial ischemia protection have been reported. The protective effects mediated by activation of adenosine receptors can be rendered by administration of adenosine. However, administering efficacious amounts of adenosine to attain the beneficial effects has been hampered by the insurmountable obstacle of the side effects of adenosine and has hindered a practical therapy based on the administration of adenosine. We hypothesized that administering the invented AC composition would allow administration of effective dosages of adenosine to attain the desirable beneficial effects in the heart and the lungs while attenuating the undesirable side effects of administering adenosine or catecholamine alone.

The pathogenesis of the catecholamine-induced myocardial necrosis has been the subject of many research papers. The cardiotoxicity effects of excessive catecholamines are well known. Sustained infusions or excessive doses of catecholamines administered to experimental animals produce myocardial dysfunction, ischemic lesions, necrosis and in addition, hemorrhagic pulmonary congestion, edema and ultimately death. This experimental model has had wide acceptance to prove the protective effects of various drugs, and has clinical relevance in syndromes including myocardial ischemia, infarction and pulmonary edema. Opioids are believed to attenuate the cardiovascular responses to surgical stress. It is thought that the cardio-pulmonary detrimental effects of catecholamines can be suppressed by opioids. Thus, the use of high doses of opioids including sufentanil is a common practice in cardiopulmonary bypass surgery. The study was undertaken to determine whether the present ACB composition could prevent cardiac damage, pulmonary edema and death induced by challenging rabbits with high doses of catecholamines. The effects were compared to those of sufentanil.

Materials and Methods

Drugs

For Protocol A: ACB (Adenosine-Catecholamine-Benzodiazepine) Composition: A=adenosine: 100 mg/kg, C=norepinephrine: 0.1 mg/kg, B=midazolam: 1 mg/kg. sufentanil: 15 µg/kg (Janssen Pharmaceutica, Titusville, N.J.).

For Protocol B: Epinephrine ratio to Adenosine or ATP was 1/160, 8-PT (8-phenyltheophylline) 25 mg/kg from Research Biochemicals International, Natick, Mass.

Unmedicated, healthy adult New Zealand white rabbits of either sex, weighing 2.5-2.7 kg were studied and the preparation was done as in Example 1. After the prepared and tracheotomized rabbits were placed in the sling with all the monitoring in place, the hemodynamic blood gas and metabolic parameters were measured for the control values. There were two experimental protocols. The protective effects of the present composition, AC, were compared with those of sufentanil and saline (control) in Protocol A, and with those of saline (control) and 8-PT in Protocol B. The adverse functional effects of catecholamines, norepinephrine (NE) and epinephrine (Epi) were studied in the in vivo animal experimental model. This was done by a continuous infusion into the marginal ear vein of high doses of the above catecholamines which provided cardiotoxic stimulation. The infusion of the drugs was slowly done in spontaneously breathing rabbits except for the sufentanil group in which ventilation-was mechanically controlled. Using a Travenol Flo-Gard 8000 volumetric infusion pump, the catecholamines, NE or Epi were continuously infused into the marginal ear vein for two and three hours respectively.

Protocol A

The study was divided in two groups, both groups received high doses of two hours continuous infusion of norepinephrine (NE) as a cardiotoxic stimulant. In Group I, the rabbits were subjected to 20 µg/kg/min (NE), and in Group II, the rabbits were subjected to 40 µg/kg/min (NE). In each group, the animals were randomly assigned to a subgroup (n=6 for each subgroup): a) Saline, b) sufentanil, c) ACB composition. All of the studied drugs (saline, sufentanil, ACB composition) were given as a pre-treatment drug prior to starting the NE infusion. Midazolam was used to sedate the animals in order to avoid excitation due to discomfort during administration of the drugs.

Protocol B

In this study, the animals were subjected to 10 µg/kg/min of Epi as a cardiotoxic stimulant. In the AC and ATPC groups, epinephrine and adenosine or ATP were mixed at a ratio of 1/160. The mixed solutions were continuously infused for 3 hours. At the beginning of the infusion, the doses were titrated to the cardiovascular responses, and gradually increased. The animals were randomly assigned in subgroups of a) saline (n=6), b) 8-PT (n=6) , AC (Adenosine/epinephrine), (n=8) , ATPC (ATP/epinephrine: n=2). In order to antagonize the endogenous adenosine, 8-PT (8-phenyltheophylline), an adenosine receptor antagonist as used.

Results and Conclusion

Figure 7A:
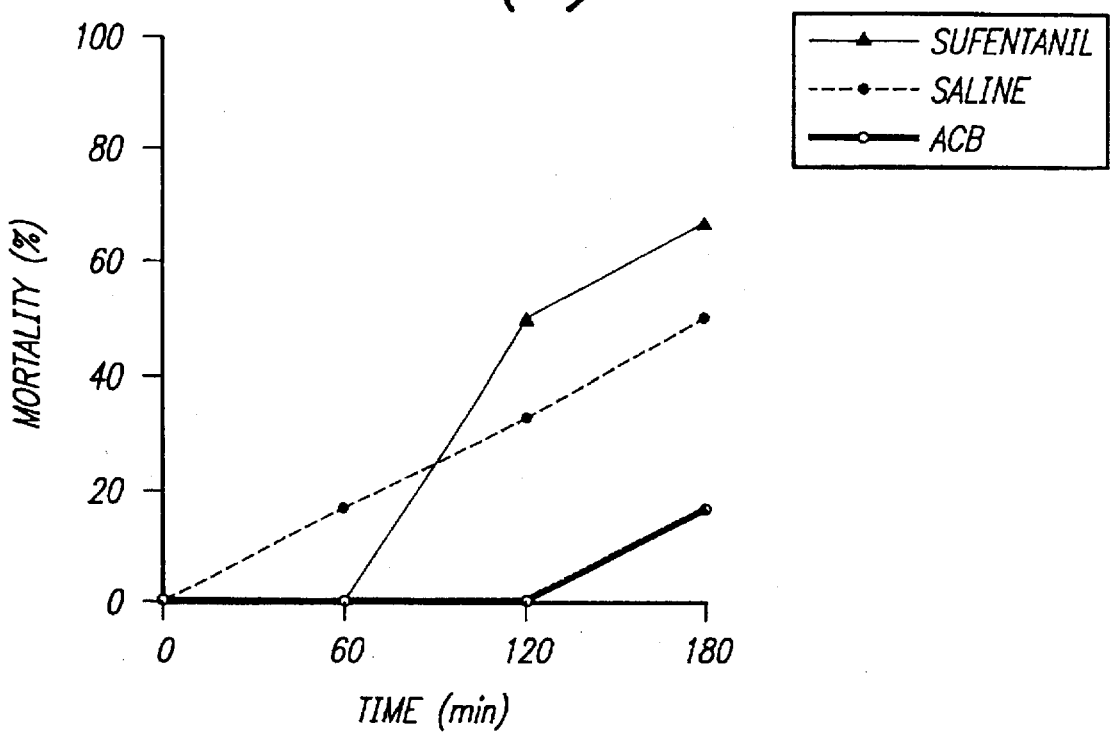
FIGS. 7(a)-(d) illustrate the rates of mortality and pulmonary edema over time due to infusion of norepinephrine as a cardiotoxic stimulant with and without adenosine/catecholamine compositions of the invention, showing the cardiopulmonary protective effects of adenosine/catecholamine compositions of the invention.
Figure 7B:
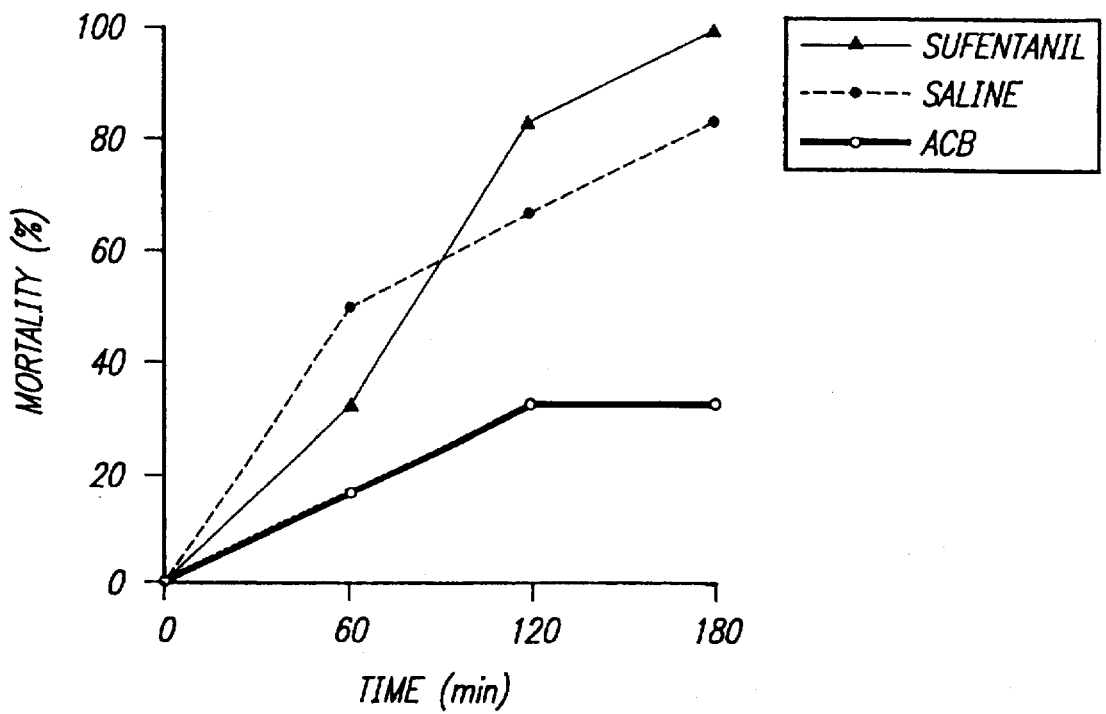
Figure 7C:
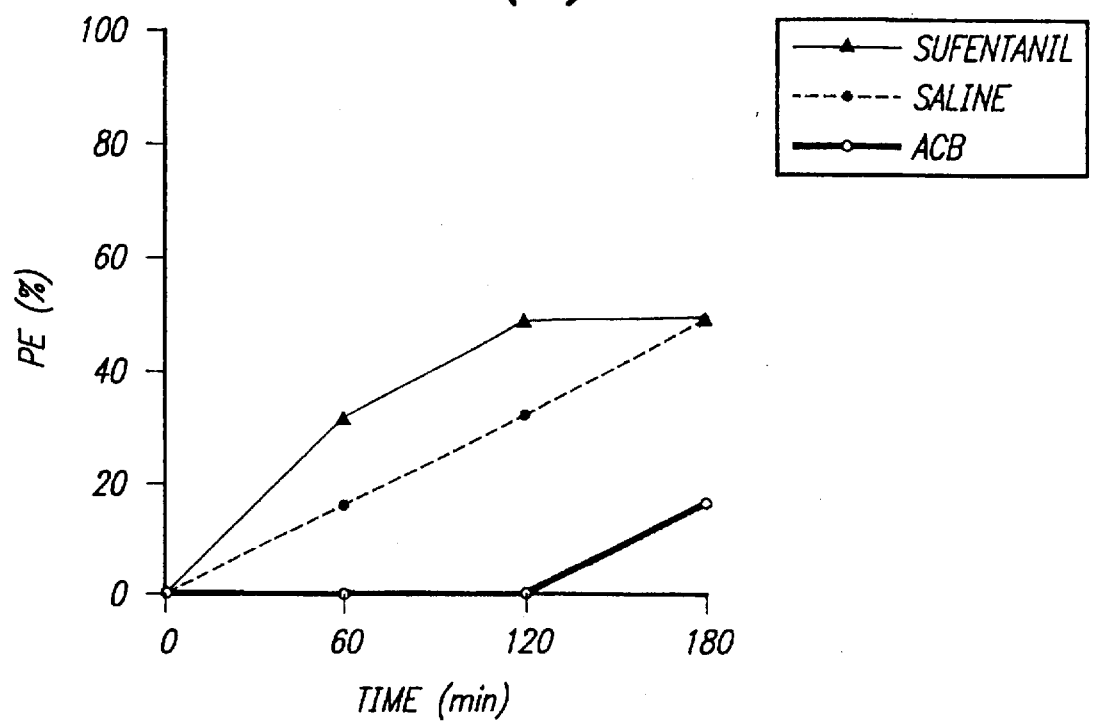
Figure 7D:
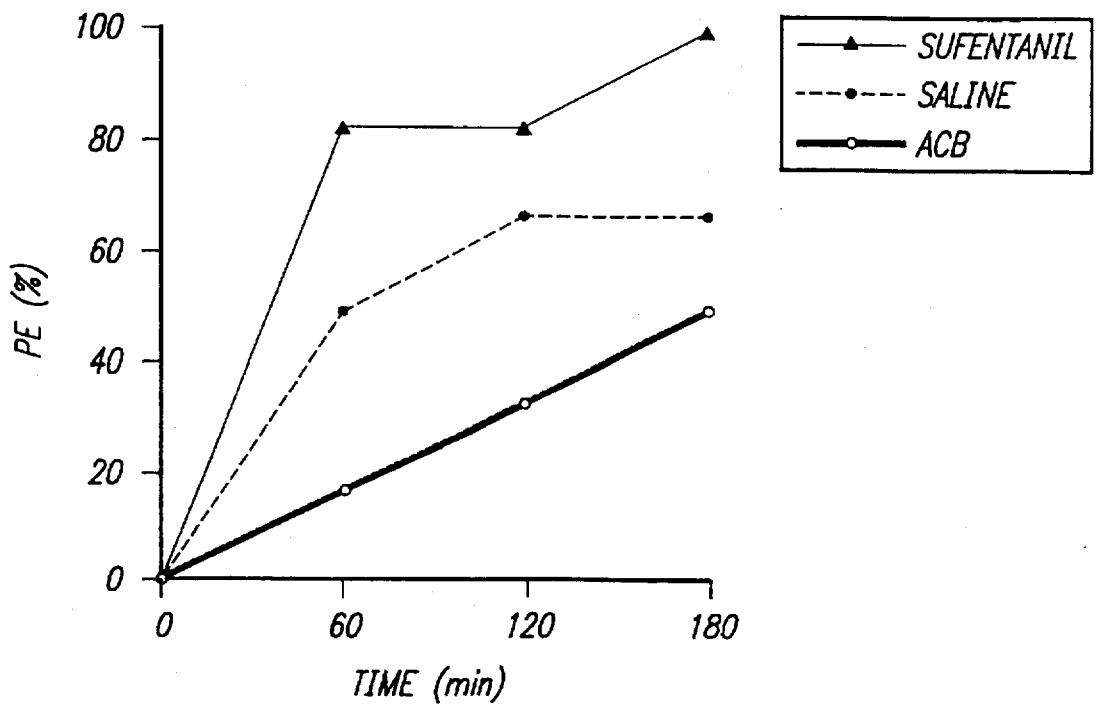

The results for Protocol A are summarized in FIG. 7(a)–(d). FIGS. 7(a) and 7(b) illustrate the mortality rate, and FIGS. 7(c) and 7(d) illustrate the rate that developed pulmonary edema (PE) when rabbits in Group I, FIGS. 7(a) and 7(c), were subjected to 20 µg/kg/min NE, and rabbits in Group II, FIGS. 7(b) and 7(d), were subjected to 40 µg/kg/min NE. The figures show that in Group II, FIG. 7(b) and (d), where higher doses of NE (40 µg/kg/min) were infused, 6/6, 100% of the animals died in the sufentanil group, 5/6 or 83% in the saline, and 2/7 or 28% in the ACB group died within 3 hours. In the Group I, FIG. 7(a) where the animals were challenged by 20 µg/kg/min of NE, all the ACB pretreated animals survived (100%) for two hours, and one died after 150 minutes. Compared to the saline group where the mortality rate was 3/6 (50%) or the sufentanil group where the mortality rate was 4/6 (67%) within 180 minutes. The number of animals that developed pulmonary congestion and edema are also much higher in the saline or sufentanil groups than in the group administered with the ACB composition (FIG. 7(c)–(d)). The blood gas data was progressively deteriorated in both the saline and sufentanil groups. However, no significant blood gas and metabolic changes were shown in the survived animals of the ACB groups.

Figure 8A:
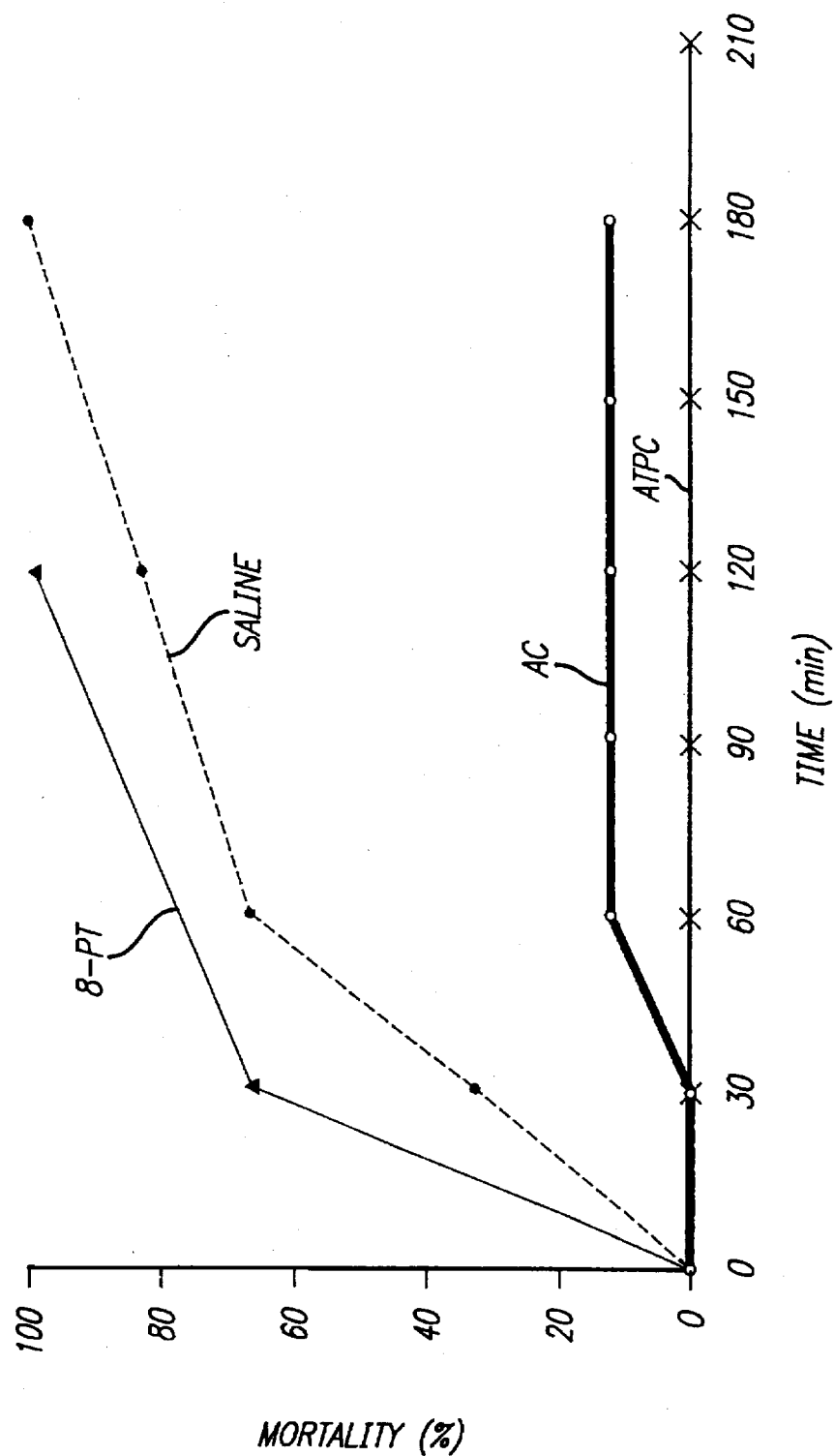
FIGS. 8(a)-(b) illustrate the rates of mortality and pulmonary edema over time due to infusion of epinephrine as a cardiotoxic stimulant with and without adenosine/catecholamine or ATP/catecholamine compositions of the invention, showing the cardiopulmonary protective effects of adenosine/catecholamine compositions of the invention.
Figure 8B:
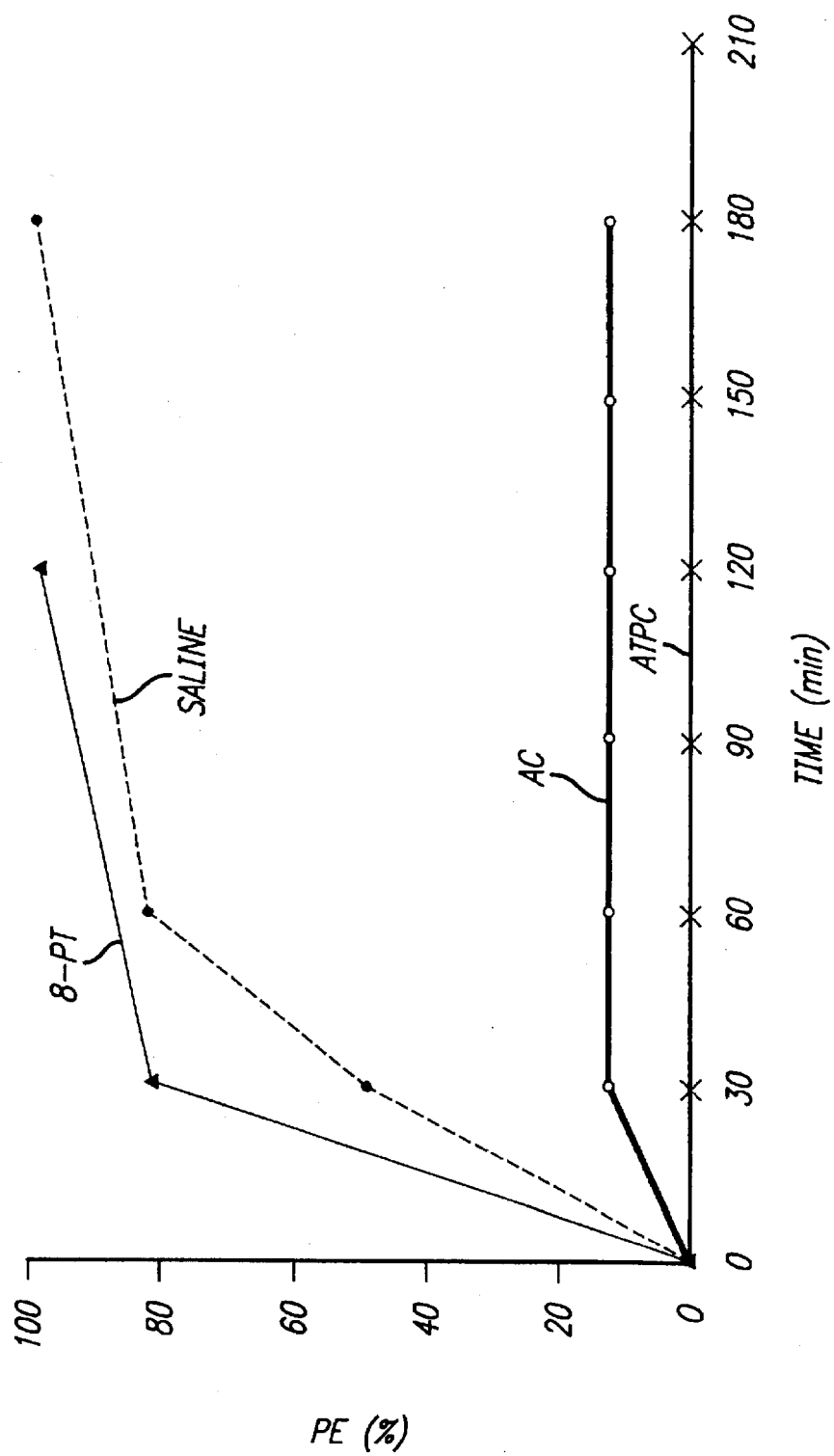

The results are summarized in FIG. 8(a)–(b) for Protocol B in which animals were challenged by high doses of Epi. FIG. 8(a) shows the mortality rate, and FIG. 8(b) shows the rate of rabbits that developed pulmonary edema (PE). As can be seen from FIGS. 8(a) and (b), almost 70% of the animals developed pulmonary edema and died within 30–60 minutes in the 8-PT and saline groups. In contrast, administration of the present composition, AC or ATPC could effectively prevent the development of pulmonary edema and death in most of the studied animals. The myocardial and pulmonary ischemic insult appeared to be involved in the catecholamine-induced damage and death which was apparent in the ECG and blood gas changes. The above results clearly demonstrate that administration of the present composition, AC, ACB or ATPC resulted in a significant reduction of pulmonary congestion and edema as well as cardiovascular damage and death in both protocols. The present composition effectively protected the heart and the lungs during acutely induced stressful and cardiotoxic stimulation challenged by large doses of catecholamine infusions.

EXAMPLE 5

Metabolic Homeostasis Maintaining and Protection of Ischemia by Administration of the AC Composition Homeostasis, the biologic responses necessary to maintain a steady state in the internal environment, is necessary for survival. Maintenance of the body's internal milieu is the major function of buffering systems, while oxygen transport and the successful preservation of aerobic metabolism are key components in maintaining cellular integrity. As normal aerobic metabolism is compromised or as the ratio of buffering elements is altered, disturbances in acid-base homeostasis occur. Lactate accumulation in extracellular fluid is due to an imbalance between oxygen supply and metabolic demand. Lactic acidosis is associated with tissue hypoxia and impaired oxidative metabolism. Tissues that normally can use oxygen to produce ATP from glucose will resort to the less energy-efficient glycolytic pathway if oxygen is unavailable. Under anaerobic conditions, lactate production will therefore increase, and since lactate is readily diffusible across cell membranes, the concentration of lactate in the blood will increase. This is the basis of blood lactate as a marker of tissue ischemia/hypoxia. A practical indicator is the hydrogen ion level as expressed in base excess (BE) determined by the arterial blood sample.

Lactic acidosis is a metabolic derangement associated with a variety of pathological states including excessive levels of stress caused by intense stimulation like major body injury, surgical or accidental. The degree of increase in the lactate level seems to correlate directly with the severity of levels of stress. Moreover, increases in lactate may reflect increased activity of the sympathetic nervous system and increase catecholamine release due to stress. Thus, responses to excess lactate are believed directly related to activation of the sympathetic nervous system after a variety of stresses, including anxiety, hypotension and major injuries. The degree of sympathetic nervous system activity and consequent release of endogenous catecholamines can directly influence the responses observed, since both epinephrine and norepinephrine result in increased blood levels of lactate and increased rates of anaerobic glycolysis in many tissues/organs. These considerations are particularly relevant in considering the responses to ischemia, hypoxia, anesthesia, surgery, hemorrhage, trauma and shock which are so dependent upon sympathetic nervous system activation and release of catecholamines.

Severe stress caused by stimuli such as surgical intervention induces acute disorders in endocrine, hormonal and cardiovascular systems. For example, traction and manipulation of the viscera during abdominal surgery in addition to the general biologic response to stress are known to be associated with marked increase in circulating catecholamines, mesenteric vasoconstriction and a decrease in gastrointestinal blood flow which may cause ischemia-reperfusion injury in various splanchnic organ systems, resulting in compromised organ function and increase in lactate levels (lactic acidosis). We designed an experimental model that can mimic the above conditions of intense sympathetic activation, release of catecholamines, severe vasoconstriction that may be transient but likely to cause ischemia-reperfusion injury in the splanchnic organ/tissues. This could be induced by delivering stressful intra-abdominal electrical stimulation. The stress response to noxious stimulation further yields a subsequent increase in oxygen demand which would worsen the imbalance of oxygen supply/demand. The measurement of blood gas/acid-base metabolic status as a useful tool in the assessment of critically ill patients and patients undergoing severe stress like trauma or surgery is well recognized. For example, elevation of blood lactate level often alerts the clinician for the need to rapidly institute appropriate monitoring and potentially lifesaving therapy.

It is thought that adenosine acting via adenosine receptor activation can play a homeostatic role, that adenosine functions as a retaliatory metabolite in response to tissue trauma, hypoxia and ischemia. Under such conditions, tissue levels of adenosine are markedly increased because of ATP breakdown. It is also believed that the anti-adrenergic effects of adenosine can be beneficial to inhibit detrimental sympathetic activation and that administration of adenosine could be beneficial. Therefore, we sought to determine whether the invented AC (adenosine/norepinephrine) composition could attenuate or prevent the metabolic disturbances caused by stressful noxious stimuli in the intestine, and inhibit the sympathetic responses which may lead to mesenteric vasoconstriction with subsequent ischemia-reperfusion injury.

Methods and Materials

Drugs: AC (Adenosine/norepinephrine ratio: 800/1 dissolved in saline) AC infusion, adenosine: 400 µg/kg/min; 8-phenyltheophylline (8-PT): 25 mg/kg; glibenclamide: 15 mg/kg.

Figure 9:
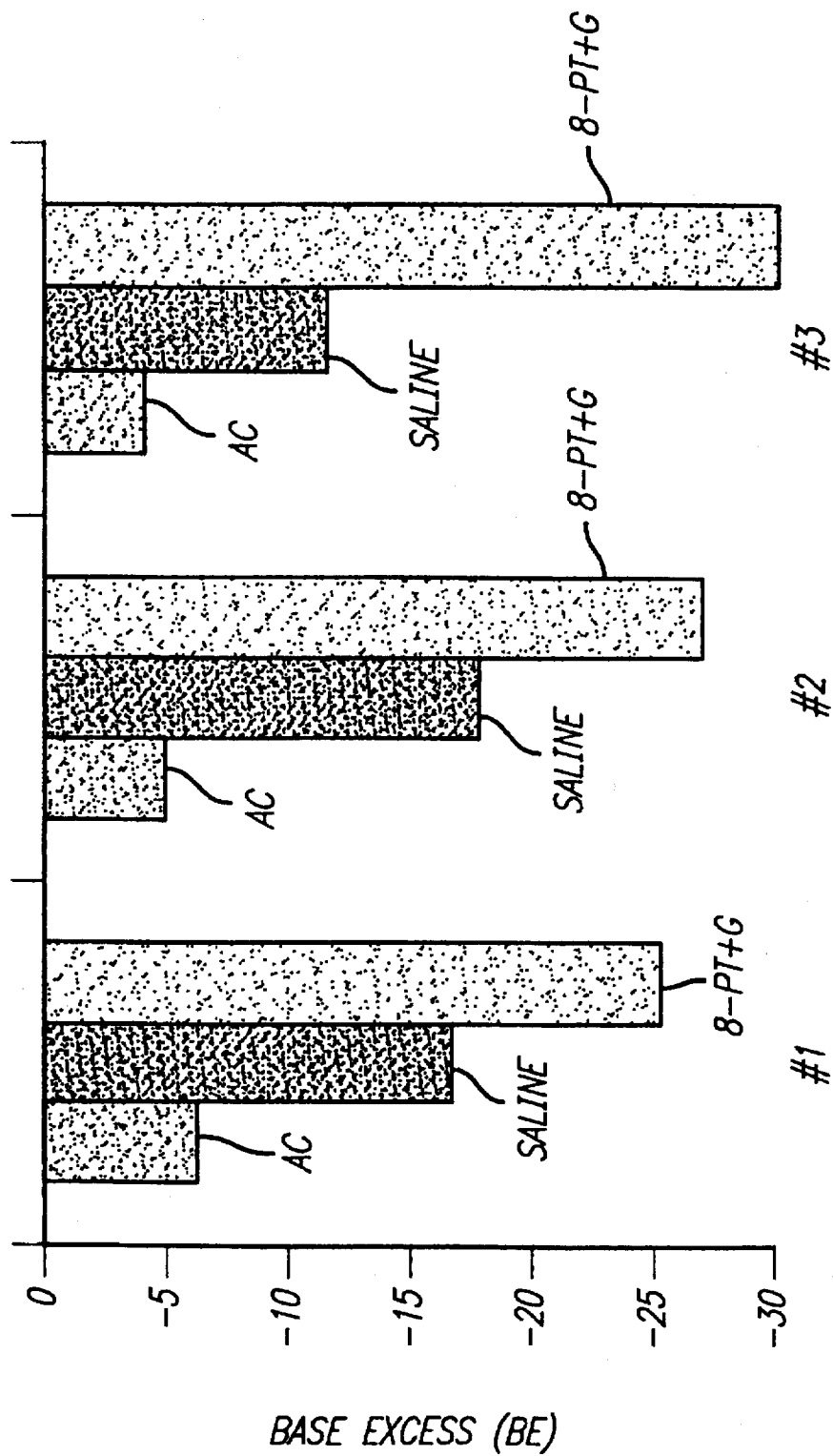
FIG. 9 is a chart illustrating effects on metabolic acidosis due to stress and the effects on maintaining metabolic homeostasis and protection from ischemia by administration of adenosine/catecholamine compositions of the invention.

The preparation of the animals was done as in Example 1. The prepared and tracheotomized rabbits were placed in a sling which allowed easy observation of the behavioral responses without restraining the animals. The cardiovascular, respiratory and metabolic monitoring was instituted. The baseline control values were then taken. EKG and hemodynamic changes were continuously monitored throughout the experiments. In addition, intermittent blood gases and the metabolic changes were measured before and after noxious stimulations. The electrical stimulation was applied at 20 minutes intervals (3 series). As is illustrated in FIG. 9, three groups of rabbits were studied: a) AC group (n=5), b) saline group (n=7); c) 8-PT+glibenclamide group (n=5). In group (c), 8-PT and glibenclamide were used in order to block endogenous release of adenosine and its effects on ATP sensitive K ion channels. 8-PT is an adenosine receptor antagonist, and Glibenclamide is an ATP-dependent K+ channel blocker. In group (c) 8-PT was administered first, and after 15 minutes, Glibenclamide was administered. In all the 3 groups (a,b,c), anesthesia was maintained with 1.4% isoflurane throughout all the experiments. In groups (a) and (b), noxious electrical visceral stimulation (EVS) was applied after 1 hour continuous infusion of AC, (adenosine, 400 µg/kg/min) or saline. The AC infusion was continued throughout the tested stimulation (EVS #1–#3). Electrical current was delivered through a nerve stimulator via electrodes that were introduced into the rectum about 10–13 cm. Electric current at predetermined intensities of 50 Hz, 80 volts were applied for 40 seconds. Behavioral responses such as bodily movement and the hemodynamic responses were carefully monitored and recorded. The blood gas variables were measured right after stimulation and every 5 minutes afterwards.

Results and Conclusion

Despite the fact that the animals were anesthetized with 1.4% isoflurane, when high intensity electric current was delivered, there was marked increase in blood pressure, heart rate, and the animals hyperventilated. The animals also moved violently, particularly in the saline and 8-PT+ Glibenclamide groups. In contrast, these behavioral and the hemodynamic responses were quite inhibited in the AC group. As FIG. 9 shows, the metabolic acidosis (decrease in BE) was progressively deteriorated and exaggerated particularly in the 8-PT+glibenclamide group (c), where the endogenous adenosine release and the $K_{ATP}$ channel activities were blocked. The metabolic conditions of these animals progressively worsened as time passed, after each stimulation (See FIG. 9), and ultimately all the animals died in group (c). In comparison, the metabolic disturbances (decrease in BE) in the AC group were minimal, and did not show any pathological condition. Twenty minutes after the last stimulation (EVS #3), the AC group animals completely recovered to normal ranges.

The results indicate that intravenous administration of the present AC composition effectively inhibited excessive sympathetic activities and mesenteric vasoconstriction caused by intense noxious stimulation, and could greatly attenuate metabolic derangements in the animals exposed to severe stressful conditions. Therefore, it can be concluded that protection against trauma and subsequent ischemia-reperfusion injury in the splanchnic organs/tissues occurred.

Although the above example was indirectly assessing splanchnic organs/tissues ischemia-reperfusion injury possibly caused by the traumatic stimulation and excessive visceral vasoconstriction, the present method is expected to be applicable to any tissue/organ that has suffered from ischemic/hypoxic damage. In addition, the AC composition is expected to be useful in critically ill patients where lactic acidosis is common and is usually caused by inadequate tissue perfusion that does not meet metabolic demand. The present composition may be beneficial to aid metabolic adjustments following accidental trauma. The present method may also be beneficial to accelerate general recovery in patients in the ICU (Intensive Care Unit). The present method is also expected to be applicable to other situations which include but are not limited to: stroke, in vivo organ preservation and transplant, trauma and shock Which results from poor circulatory conditions, and a variety of pathological states resulting from metabolic disturbances.

EXAMPLE 6

Intravenous Administration of a Combination of Adenosine Analog (R-PIA)-Catecholamine Unmedicated, healthy New Zealand white rabbits were prepared as in Example 1. Anesthesia was maintained with isoflurane 1.4% throughout all the experiments. A mixture of 5.0 mg. of an adenosine analog compound, R(−) $N^6$-(2-phenylisopropyl) adenosine (R-PIA) and 0.1 mg of norepinephrine (NE) was administered by intravenous infusion over a period of about 10 minutes. The initial blood pressure of about 100 mmHg gradually dropped during the infusion. When the initial infusion was stopped, blood pressure began to fall, as the norepinephrine was metabolized more quickly than the R-PIA, and resulting in increased hypotension. To counter this hypotensive condition, a separate continuous infusion of 4 µg/kg/min of norepinephrine (NE) was administered for a period of about 5 minutes to support blood pressure at about 75–80 mmHg, followed by administration of a continuous infusion of 2 µg/kg/min of norepinephrine to maintain and stabilize blood pressure near normotensive levels. The results of the initial infusion of the mixture of R-PIA and norepinephrine, followed by a staged, separate continuous infusion of norepinephrine are shown in the blood pressure tracing of FIG. 10.

EXAMPLE 7

Intravenous Administration of a Combination of Adenosine Analog (R-PIA)-Catecholamine Unmedicated, healthy New Zealand white rabbits were prepared as in Example 1. Anesthesia was maintained with isoflurane 1.4% throughout all the experiments. A mixture of 5.0 mg. of an adenosine analog compound, R(−)$N^6$-(2-phenylisopropyl)adenosine (R-PIA) and 0.1 mg of norepinephrine was initially administered by intravenous infusion over a period of about 13 minutes, as in Example 6. However, administration of a separate continuous infusion of 4 µg/kg/min of norepinephrine (NE) was begun about halfway through the initial infusion of the mixture, and was continued for a period of about 10 minutes to stabilize blood pressure. This was followed by reduction of the continuous infusion of norepinephrine to 2 µg/kg/min to maintain and stabilize blood pressure near normotensive levels. The results of the initial infusion of the mixture of R-PIA and norepinephrine, accompanied by a staged, separate continuous infusion of norepinephrine, are shown in the blood pressure tracing of FIG. 11.

EXAMPLE 8

Intravenous Administration of a Combination of Adenosine Analog (NECA)-Catecholamine Unmedicated, healthy New Zealand white rabbits were prepared as in Example 1. Anesthesia was maintained with isoflurane 1.4% throughout all the experiments. A mixture of 1.25 mg. of an adenosine analog compound, 5'-N-ethylcarboxamidoadenosine (NECA) and 0.2 mg of norepinephrine (NE) was initially administered by intravenous infusion over a period of about 13 minutes. Administration of a separate continuous infusion of 60 µg/kg/min of norepinephrine (NE) was begun about 1–2 minutes following the commencement of infusion of the mixture, and was continued to maintain and stabilize blood pressure at normotensive levels. The results of the initial infusion of the mixture of NECA and norepinephrine, accompanied by a separate continuous infusion of norepinephrine, are shown in the blood pressure tracing of FIG. 12.

While the principles and exemplary embodiments of the present invention have been discussed herein, many variations and modifications can be made to the invention as disclosed without departing from the spirit and scope of the invention.

We claim:

1. An in vitro pharmaceutical composition capable of inducing or maintaining one or more desired effects selected from the group consisting of anesthesia, analgesia, and ischemia protection, said composition comprising a purine compound and a catecholamine compound in a pharmaceutically acceptable carrier, wherein said purine compound is selected from the group consisting of adenosine, phosphorylated adenosine, 5'-N-ethylcarboxamidoadenosine, R(−) $N^6$-(2-phenylisopropyl) adenosine, 2-chloroadenosine, $N^6$-cyclopentyladenosine, and $N^6$-cyclohexyladenosine; and said catecholamine compound is selected from the group consisting of epinephrine, norepinephrine, dopamine, dobutamine, ephedrine, methoxamine, and phenylephrine;

wherein administration of said in vitro composition to a mammal in an amount sufficient to induce or maintain one or more of said desired effects will not reduce blood pressure to the same degree blood pressure would be reduced in the absence of said catecholamine; wherein:

when said purine compound is adenosine, and when said catecholamine compound is norepinephrine, said combination comprises about one part by weight norepinephrine to about 25 to about 2000 parts by weight purine compound;

when said catecholamine compound is epinephrine, said combination comprises about one part by weight epinephrine to about 50 to about 4000 parts by weight purine compound;

when said catecholamine compound is phenylephrine, said combination comprises about one part by weight phenylephrine to about 10 to about 200 parts by weight purine compound; and when said catecholamine compound is dopamine, said combination comprises about one part by weight dopamine to about 2 to about 5 parts by weight purine compound, wherein an amount of said composition sufficient to induce one of said desired effects would cause hypotension in the absence of said catecholamine.

* * * * *

UNITED STATES PATENT AND TRADEMARK OFFICE
CERTIFICATE OF CORRECTION

PATENT NO. : 5,679,650
DATED : Oct. 21, 1997
INVENTOR(S) : Atsuo F. Fukunaga, et al It is certified that error appears in the above-identified patent and that said Letters Patent is hereby corrected as shown below:

Cover Page, "Inventors", change "Funuknaga", to read --Fukunaga--.

Column 1, line 11, change "08/003,214", to read --08/083,214--.

Column 22, line 53, change "Glibenclamide", to read --glibenclamide--.

Column 23, line 8, change "Glibenclamide", to read --glibenclamide--.

Signed and Sealed this

Sixteenth Day of June, 1998

Attest:

BRUCE LEHMAN

Attesting Officer

Commissioner of Patents and Trademarks